(12) United States Patent
Ilan et al.

(10) Patent No.: US 9,717,754 B2
(45) Date of Patent: *Aug. 1, 2017

(54) GLUCOCEREBROSIDE TREATMENT OF DISEASE

(75) Inventors: Yaron Ilan, Jerusalem (IL); Maya Margalit, Jerusalem (IL); Ari Zimran, Jerusalem (IL)

(73) Assignee: Enzo Therapeutics, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 10/675,980

(22) Filed: Sep. 30, 2003

(65) Prior Publication Data

US 2004/0171557 A1 Sep. 2, 2004

(51) Int. Cl.
| | |
|---|---|
| *A61K 38/00* | (2006.01) |
| *A61K 31/739* | (2006.01) |
| *A61K 31/70* | (2006.01) |
| *A61K 31/7032* | (2006.01) |
| *A61K 38/17* | (2006.01) |
| *A61K 31/00* | (2006.01) |
| *A61K 31/7004* | (2006.01) |
| *A61K 31/7028* | (2006.01) |
| *A61K 35/15* | (2015.01) |
| *A61K 35/17* | (2015.01) |

(52) U.S. Cl.
CPC ............ *A61K 31/739* (2013.01); *A61K 31/00* (2013.01); *A61K 31/70* (2013.01); *A61K 31/7004* (2013.01); *A61K 31/7028* (2013.01); *A61K 31/7032* (2013.01); *A61K 35/15* (2013.01); *A61K 35/17* (2013.01); *A61K 38/1709* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,598,051 A | | 7/1986 | Papahadjopoulos et al. |
| 5,101,026 A | * | 3/1992 | Ogawa et al. .................. 536/53 |
| 5,709,879 A | | 1/1998 | Barchfield et al. |
| 5,747,463 A | * | 5/1998 | Marinier et al. ................ 514/25 |
| 5,861,520 A | | 1/1999 | Ogawa et al. |
| 5,869,048 A | * | 2/1999 | Das ........................... 424/141.1 |
| 5,942,237 A | * | 8/1999 | Gizurarson et al. ....... 424/278.1 |
| 6,043,339 A | | 3/2000 | Lin et al. |
| 6,280,774 B1 | | 8/2001 | Rang et al. |
| 6,355,626 B1 | | 3/2002 | Panettieri et al. |
| 6,610,835 B1 | * | 8/2003 | Liotta et al. ................... 536/4.1 |
| 6,756,208 B2 | * | 6/2004 | Griffin et al. ................... 435/13 |
| 6,756,504 B2 | | 6/2004 | Dagan et al. |
| 7,897,580 B2 | | 3/2011 | Ilan |
| 2002/0141977 A1 | * | 10/2002 | Collins et al. ............... 424/93.7 |
| 2003/0157135 A1 | | 8/2003 | Tsuji et al. |
| 2003/0170258 A1 | | 9/2003 | Roy-Chowdhury et al. |
| 2004/0022768 A1 | | 2/2004 | Roy-Chowdhury et al. |
| 2004/0023909 A1 | | 2/2004 | Roy-Chowdhury et al. |
| 2004/0087485 A1 | | 5/2004 | Ilan et al. |
| 2004/0171522 A1 | | 9/2004 | Ilan et al. |
| 2004/0171526 A1 | | 9/2004 | Ilan et al. |
| 2004/0171527 A1 | | 9/2004 | Ilan et al. |
| 2004/0171528 A1 | | 9/2004 | Ilan et al. |
| 2004/0171557 A1 | | 9/2004 | Ilan et al. |
| 2006/0116331 A1 | | 6/2006 | Jiang et al. |
| 2007/0010483 A1 | * | 1/2007 | Ilan et al. ....................... 514/54 |
| 2007/0117778 A1 | * | 5/2007 | Ilan ................................ 514/54 |
| 2009/0221516 A1 | | 9/2009 | Tashiro et al. |

FOREIGN PATENT DOCUMENTS

| | | |
|---|---|---|
| EP | 0957161 | 11/1999 |
| EP | 0988860 | 3/2000 |
| WO | WO 9933475 | 7/1999 |
| WO | WO01/79152 | 10/2001 |
| WO | WO 02/051986 | 7/2002 |
| WO | WO03/009812 | 2/2003 |
| WO | WO03/027058 | 4/2003 |
| WO | WO 03093287 | 11/2003 |
| WO | WO2005/032462 | 4/2005 |
| WO | WO2007/099999 | 9/2007 |

OTHER PUBLICATIONS

Smyth et al (2002) Current Opinion in Immunology. 14: 165-171.*
Vliet et al (1999) Immunology. 98: 557-563.*
Connolly and Cunningham (2000) European Journal of Anaesthesiology. 17:219-220.*
Makowska et al (2000) Scand. J. Immunol. 52: 71-79.*
Degroote et al. The cell biology of glycosphingolipids. Sem in Cell & Dev Bio, 2004. 15: 375-387.*

(Continued)

*Primary Examiner* — Michelle S Horning
(74) *Attorney, Agent, or Firm* — Paul Diamond, Esq.

(57) ABSTRACT

The present invention provides a method for the treatment of immune mediated or immune related diseases or disorders, infectious diseases, metabolic disorders and cancer in mammalian subjects. This method comprises the administration of a naturally occurring, mammalian intermediary metabolite or T cell receptor ligand, preferably a glucosylceramide, to a mammalian subject. In a preferred embodiment, such mammalian subjects are human beings.

16 Claims, 21 Drawing Sheets

(56) References Cited

OTHER PUBLICATIONS

Sweeley. Glycosphhingolipids: structure and function. Pure & Appl. Chem. 1989. 61(7): 1307-1312.*
Belchetz et al. Treatment of Gaucher's Disease with Liposome-Entrapped Glucocerebroside: beta-Glucosidase. Lancet. Jul. 16, 1977; 2(8029):116-7.*
Adar and Ilan. β-Glycosphingolipids as Immune Modulators. Journal of Immunotoxicology. 2008, vol. 5, No. 2 , pp. 209-220.*
Lengle et al. Arterial thrombosis in ulcerative colitis. Transcatheter thrombolytic therapy. West J Med. Jun. 1995; 162(6): 543-547.*
Maragoudakis et al. Effects of thrombin/thrombosis in angiogenesis and tumour progression. Matrix Biol. Aug. 2000;19(4):345-51. Review.*
Marra et al. Expression of the thrombin receptor in human liver: up-regulation during acute and chronic injury. Hepatology. Feb. 1998;27(2):462-71.*
Brunt et al. Nonalcoholic steatohepatitis: a proposal for grading and staging the histological lesions.Am J Gastroenterol. Sep. 1999;94(9):2467-74.*
Bleicher, P.A., et al., "Expression of murine CD1 on gastrointestinal epithelium," Science 250:679-682 (1990) [Exhibit 1].
Ilan, et al.. U.S. Appl. No. 10/451,811, filed Jun. 25, 2003, published in International Patent Application No. WO 25/051986, filed Dec. 24, 2001 [Exhibit 3].
Ilan, et al., U.S. Appl. No. 10/375,906, filed Feb. 27, 2003 [Exhibit 4].
Roy-Chowdhury, et al; U.S. Appl. No. 08/808,629, filed Feb. 28, 1997, specification almost present in divisional applications U.S. Appl. No. 10/377,628, filed Mar. 4, 2003, U.S. Appl. No. 10/377,603, filed Mar. 4, 2003, and U.S. Appl. No. 09/447,704, filed Feb. 28, 1997 [Exhibit 8].
Roy-Chowdhury, et al, U.S. Appl. No. 09/356,294, filed Jul. 16, 1999 and U.S. Appl. No. 10/385,440, filed May 9, 2001, specifications of both published on Sep. 11, 2003 as U.S. Appl. No. 2003-0170258 [Exhibit 9].
Vicari, A.P., et al., "Mouse NK1.1 + T cells: a new family of T cells," Immunology Today 17(2):71 (1996) [Exhibit 12].
Margalit, M., et al., "Glucocerebroside Treatment Ameliorates Con-A Hepatitis by Inhibition of NKT Lymphocytes: A New Immunemodulatory Tool," Hepatology 38:163A (2003).
U.S. Appl. No. 10/375,906, filed Mar. 4, 2003, Ilan et al.
U.S. Appl. No. 08/808,629, filed Feb. 28, 1997, Roy-Chowdhury, et al.
Bleicher, P.A., et al., "Expression of murine CD1 on gastrointestinal epithelium," Science 250:679-682 (1990).
Collins, C., et al., "RAG1, RAG2 and pre-T cell receptor alpha chain expression by adult human hepatic T cells: evidence for extrathymic T cell maturation," Eur. J. Immunol. 26:3114-3118 (1996).
Madsen, K.L., et al., "Interleukin 10 prevents cytokine-induced disruption of T84 barrier integrity and limits chloride secretion," Gastroenterology 113:151-159 (1997).
Mitchell, D.G., et al., "Fatty liver. Chemical shift phase-difference and suppression magnetic resonance imaging techniques in animals, phantoms, and humans," Invest. Radiol. 26:1041-1052 (1991).
Namimoto, T., et al., "Adrenal Masses: Quantification of Fat Content with Double-Echo Chemical Shift In-Phase and Opposed-Phase Flash MR Images for Differentiation of Adrenal Adenomas," Radiology 218:642-646 (2001).
Sullards, M.C., et al., "Structure determination of soybean and wheat glucosylceramides by tandem mass spectrometry," J. Mass Spectrometry 35:347-353 (2000).
Trop, S., et al., "Liver-Associated Lymphocytes Expressing NK1.1 Are Essential for Oral Immune Tolerance Induction in a Murine Model," Hepatology 29:746-755 (1999).
Vicari, A.P., et al., "Mouse NK1.1 + T cells: a new family of T cells," Immunology Today 17(2):71 (1996).
U.S. Appl. No. 11/378,941, filed Mar. 17, 2006.

Dwek, RA., Block, TM, Nichita-Branza, N., Petrescu, S., Platt, F., Rudd, PM, Zitzmann, N., "Abnormal glycosylation in disease and therapy", Proceedings of the Royal Society of Medicine's $5^{th}$ Jenner Symposium (Glycobiology and Medicine conference), Jul. 10-11, 2000.
Axford. Glycobiology & Medicine: A millennial Review, Jul. 2000.
Beecher, WC, Metabolic profiling: Its role in biomarker discovery and gene function analysis, Chapter 17: The human metabolome. Kluwer Academic, 2003.
Margalit et al. Glucocerebroside treatment ameliorates ConA hepatitis by inhibition of NKT lymphocytes. Am. J. Physiol. Gastrointest. Liver Physiol., Nov. 2005, Abstract.
Margalit et al. Amelioration of hepatic fibrosis via beta-glucoceramide mediated immune modulation is associated with NKT lymphocyte distribution and a cytokine shift. Am. Assoc. For Study of Liver Diseases, Meeting, Nov. 2005.
Margalit et al. Suppression of hepatocellular carcinoma by glucocerebroside is associated with altered NKT and CD8+ lymphocyte distributions, stat1 expression, lack of stat6 expression and a Th1 type immune response. Am Assoc. For Disease of Liver, Oct. 200, Abstract.
Zigmond et al., Facilitation of hapatocellular carcinaoma growth in mice by double negative NKT regulatory lymphocytes is inhibited by ex vivo exposure to beta-glucosylceramide. Am Assoc. for Study of Liver Diseases, Meeting, Nov. 2005.
Knipe, DM, Howley, PM, eds. Fields virology. $4^{th}$ ed. vol. 1. Philadelphia: Lippincott Williams & Wilkins, 2001, 1004-1016 and 1127-1161.
Hahn. Subversion of immune responses by hepatitis C virus: immunomodulatory strategies beyond evasion? Current opinion in immunology, 2003, vol. 15, 443-449.
De Francesco et al., Challenges and successes in developing new therapies of hepatitis C. Nature, 2005, vol. 436, 953-960.
Schoenfeld, Y., et al, "Gaucher's disease: a disease with chronic stimulation of the immune system," Arch Pathol Lab Med 106(8):388-391 (1982).
Lichtenstein, et al, "Cytokine mRNA in Gaucher Disease," Blood Cells, Molecules and Diseases 23(19):395-401 (1997).
Barak, V., et al, "Cytokines in Gaucher's Disease," Eur. Cytokine Netw. 10(2):205-210 (1999).
Hollak, CEM, et al, "Elevated Levels of M-CSF, sCD14 and IL8 in Type 1 Gaucher Disease," Blood Cells, Molecules and Diseases 23(11):201-212 (1997).
Allen, MJ, et al, "Pro-inflammatory cytokines and the pathogenesis of Gaucher's disease: increased release of interleukin-6 and interleukin-10," Q. J. Med. 90(1):19-25 (1997).
Deibener, J., et al, "Enzyme replacement therapy decreases hypergammaglobulinemia in Gaucher's disease," Haematologica 83:479-480 (1998).
Lachman, et al, "Massive hepatic fibrosis in Gaucher's disease: clinico-pathological and radiological features," Q. J. Med 93:237-244 (2000).
Kawano, et al, "CD1d-Restricted and TCR-Mediated Activation of $V_a14$ NKT Cells by Glycosylceramides," Science 278:1626-1629 (1997).
Burdin, N., et al, "Selective Ability of Mouse CD1 to Present Glycolipids: $_a$-Galactosylceramide Specifically Stimulates $V_a14^+$ NK T Lymphocytes," J. Immunol 161:3271-3281 (1998).
Roy-Chowdhury, et al, U.S. Appl. No. 08/808,629, filed Feb. 28, 1997.
Roy-Chowdhury, et al, U.S. Appl. No. 09/356,294, filed Jul. 16, 1999, specification subsequently published in U.S. Patent Application No. 2003-0170258-A1, published Sep. 11, 2003.
Rabbani, et al, European Patent Application 1 072 271 A2, published Jan. 31, 2001.
Hollak, et al, "Marked elevation of plasma chitotriosidase activity. A novel hallmark of Gaucher disease," J. Clin. Invest. 93(3):1288-1292 (1994).
Ferrari, C., et al, "Immunopathogenesis of hepatitis C virus infection," J. Hepatol 31s1:31-38 (1999).
Cerny, A., et al, "Pathogenesis of chronic hepatitis C: immunological features of hepatic injury and viral persistence," Hepatology 30(3):595-601 (1999).

(56) References Cited

OTHER PUBLICATIONS

Rehermann, B., "Cellular immune response to the hepatitis C virus," J. Viral Hepat. 6s1:31-35 (1999).
Gotsman, I., et al, "Induction of oral tolerance towards hepatitis B envelope antigens in a murine model," Antiviral Research 48:17-26 (2000).
Akbar, SM, et al, "Low responsiveness of hepatitis B virus-transgenic mice in antibody response to T-cell-dependent antigen: defect in antigen presenting activity of dendritic cells", Immunology 78(3):468-475 (1993).
The complete listing of diseases is retrieved from http://www.mic.ki.se/Diseases/Alphalist.html.
Takahashi, M., Nakamura, K., Honda, K., Kitamura, Y., Mitzutani, T., Araki, Y., Kabemura, T., Chijiiwa, Y., Harada, N., Nawata, H., "An inverse correlation of human peripheral blood regulatory T cell frequency with the disease activity of ulcerative colitis", Dig Dis Sci. Apr. 2006 51(4): 677-86, (Abstract only).
Bode, JG., Ludwig, S., Ehrhardt, C., Albrecht, U., Erhardt, A., Schaper, F., Heinrich, PC, Haussinger, D., "IFN-alpha antagonistic activity of HCV core protein involves induction of suppressor of cytokine signaling-3", FASEB J. Mar. 2003; 17(3):488-90 Epub Jan. 22, 2003.
U.S. Appl. No. 09/447,704, filed Nov. 23, 1999, Row-Chowdhury et al.
Adar et al., "Increased red blood cell aggregation in patients with Gaucher disease is non-inflammatory," *Clinical Hemorheology and Microcirculation*, vol. 40, p. 113-118 (2008).
Adar et al., "Aggregation of red blood cells in patients with Gaucher disease," *British Journal of Haematology*, vol. 134. pp. 432-437 (2006).
Adar et al., "beta-Glycosphingolipids as Immune Modulators," *Journal of* Immunotoxicology, vol. 5, pp. 209-220 (2008).
Ajuebor et al., "Role of chemokines and chemokine receptors in the gastrointestinal tract," *Immunology*, vol. 105, pp. 137-143 (2002).
Araki et al., "Synthetic Glycolipid Ligands for Human iNKT Cells as Potential Therapeutic Agents for Immunotherapy," *Current Medicinal Chemistry*, vol. 15, pp. 2337-2345 (2008).
Axford, "Glycobiology & Medicine: A Millenial Review," *GlycoScience*, Mar. 30, 2001.
Bendelac et al., "The Biology of NKT Cells," *Annu. Rev. Immunol.*, vol. 25, pp. 297-336 (2007).
Berzofsky et al., "Progress on new vaccine strategies against chronic viral infections," *J. Clin Invest*, vol. 114, No. 4, pp. 450-462 (2004).
Bezbradica et al., "Distinct Roles of Dendritic Cells and B Cells in Va14Ja18 Natural T Cell Activation In Vivo," *The Journal of Immunology*, vol. 174, pp. 4696-4705 (2005).
Biburger et al., "Alpha-Galactosylceramide-Induced Liver Injury in Mice is Mediated by TNF-alpha but Independent of Kupffner Cells" *The Journal of Immunology*, vol. 175, pp. 1540-1550 (2005).
Brigl et al., "CD1: Antigen Presentation and T Cell Function," *Annu. Rev. Immunol.*, vol. 22 pp. 817-890 (2004).
Brutkiewicz et al., "CD1d-Mediated Antigen Presentation to Natural Killer T (NKT) Cells," *Critical Review in Immunology*, vol. 23, Nos. 5 & 6, pp. 403-419 (2003).
Brutkiewicz et al., "CD1d Ligands: The Good, the Bad, and the Ugly," *The Journal of Immunology*, vol. 177, pp. 769-775 (2006).
Chiu et al., "Multiple defects in antigen presentation and T cell development by mice expressing cytoplasmic tail-truncated CD1d," *Nature immunology*, vol. 3, No. 1, pp. 55-60 (2002).
Cohen, *Science*, vol. 285 (5424), pp. 2630 (2001).
Connolly et al., *European Journal of Anaesthesiology*, vol. 17, pp. 219-220 (2000).
Curat et al., From Blood Monocytes to Adipose Tissue-Resident Macrophages Induction of Diapedesis by Human Mature Adipocytes, *Diabetes*, vol. 53, pp. 1285-1292 (2004).
Dao et al., "Development of CD1d-restricted NKT cells in the mouse thymus," *Dur. J. Immunol.*, vol. 34, pp. 3542-3552 (2004).

Darnell et al., "Jak-STAT Pathways and Transcriptional Activation in Response to IFNs and Other Extracellular Signaling Proteins," *Science New Series*, vol. 264, No. 5164, pp. 1415-1421 (1994).
Definition of "prevention" from the Institute for International Medical Education [online], [Retrieved on Mar. 24, 2011]. Retrieved from the internet: http://www.iime.org/glossary.htm. Published Feb. 2002, p. 1, 2, 26, 27 and 39.
Degenerative nervous system diseases http://neurology.healthcares.net/degenerative-ststemphp> Jun. 26, 2005.
Degroote et al., "The cell biology of glycosphingolipids," *Semin Cell Dev Bilo*, vol. 15, No. 4, pp. 375-387 (2004).
Duwaerts et al., *Expert Opinion on Therapeutic* Targets, vol. 15, No. 8, pp. 973-988 (2011).
Epstein et al., "The SCID-hu Myeloma Model," *Methods in Molecular* Medicine, vol. 113, pp. 183-190 (2005).
Exiley et al., "To Be or Not to Be NKT: Natural Killer T Cells in the Liver," *Hepatology*, vol. 40, pp. 1033-1040 (2004).
Fernandez-Real et al., "Insulin Resistance and Chronic Cardiovascular Inflammatory Syndrome," *Endocrine Reviews*, vol. 24, No. 3 pp. 278-301 (2003).
Gatenby, et al., "The Glycolytic Phenotype in Carcinogenesis and Tumor Invasion: Insights through Mathematical Models;" *Cancer Research*, vol. 63, pp. 3847-3854 (2003).
Ghosh et al., "Targeting of liposomes towards different cell types of rat liver through the involvement of lisposomal surface glycosides," *Arch Biochem Biophys*, vol. 213, No. 1, pp. 266-270 (1982).
Godfrey et al., "Going both ways: immune regulation via CD1d-dependent NKT cells," *J. Clinical Invest.*, vol. 114. pp, 1379-1388 (2004).
Godfrey et al. "The Elusive NKT Cell Antigen—Is the Search Over?," *Science*, vol. 306, pp. 1687-1689 (2004).
Goker-Alpan et al., "Risky business: Gaucher disease and multiple myeloma," *Blood*, vol. 105 pp. 4546-4547 (2005).
Gokhan-Hotamisligil, "Inflammation and metabolic disorders," *Nature*, vol. 444, pp. 860-867 (2006).
Halder et al., "Type II NKT cell-mediated energy induction in type I NKT cells prevents inflammatory liver disease," *J. Clin. Invest.*, vol. 117, No. 8, pp. 2302-2312 (2007).
Hammond et al., "NKT cells: Potential targets for autoimmune disease therapy?," *Tissue Antigens*, vol. 59, pp. 353-363 (2002).
Hammond et al., "Natural killer T cells: natural or unnatural regulators of autoimmunity?," *Current Opinion in* Immunology, vol. 15, pp. 683-689 (2003).
Hansen et al., "Regulation of immunity and pathogenesis in infectious diseases by CD1d-restricted NKT cells," *International Journal for* Parasitology, vol. 34, pp. 15-25 (2004).
Hansen, B.C., "The Metabolic Syndrome X," *Annals New York Academy of Sciences*, vol. 892, pp. 1-24 (1999).
Hansen-Flaschen, "Update in Pulvonary Medicine," *Ann. Intern. Med.*, vol. 138, pp. 319-325 (2003).
Haratz et al., "Autoimmune hemolytic anemia in Gaucher's disease," *Journal of Molecular* Medicine, vol. 68, No. 2, pp. 94-95 (1990).
Hoffman, E.P., "Genetic Changes in Cancer: Second of three Parts" [online], [Retrieved on Apr. 14, 2011]. Retrieved from the Internet: http://www.candlelighters.org/research/genetics2.aspx.
Holland, et al., "Inhibition of Ceramide Synthesis Ameliorates Glucocorticoid-, Saturated-Fat-, and Obesity-Induced Insulin resistance," *Cell Metabolism*, vol. 5, pp. 167-179 (2007).
Hotamisligil et al., "Adipose Expression of tumor Necrosis Factor-a: Direct Role in Obesity-Linked Insulin Resistance," *Science*, vol. 259, No. 5091. pp. 87-91 (1993).
Huang et al., "Recent development of therapeutics for chronic HCV infection," *antiviral Res.*, vol. 71, pp. 351-362 (2006).
Huber et al., Role of CD1d in Coxsackievirus B3-Induced Myocarditis, *The Journal of* Immunology, vol. 170, pp. 3147-3153 (2003).
Ilan et al., "Alleviation of Acute and Chronic Graft-Versus-Host Disease in a Murine Model is Associated with Glucocerebroside-Enhanced Natural Killer T Lmyphocyte Plasticity," *Transplantation*, vol. 83, No. 4, pp. 458-467 (2007).

(56) References Cited

OTHER PUBLICATIONS

"Immune System" from Kids-Health [online]. [Retrieved Mar. 24, 2011]. Retrieved from the internet: http://kidshealth.org/teen/your_body/body_basics/immune.html. Published Jun. 18, 2007.

"Immunodeficiency Disorders" from the Merck Manual Home Edition [online]. [Retrieved Mar. 18, 2011]. Retrieved from the internet: http://www.merckmanuals.com/home/print/sec16/ch184/ch184a.html.

Jaruga et al., "Crucial Role of IL-4/STAT6 in T Cell-Mediated Hepatitis: Up-Regulating Eotaxins and IL-5 and Recruiting Leukocytes," *The Journal of Immunology*, vol. 171, pp. 3233-3244 (2003).

Kaneko et al., "Augmentation of Valpha14 NKT Cell-mediated Cytotoxicity by Interleukin 4 in an Autocrine Mechanism Resulting in the Development of Concanavalin A-induced Hepatitis," *J. Exp. Med.*, vol. 191, No. 1, pp. 105-114 (2000).

Kaneto et al., "Oxidative Stress and the JNK Pathway in Diabetes," *Current Diabetes Review*, vol. 1, pp. 65-72 (2005).

Kershaw et al., "Adipose Tissue as an Endocrine Organ," *J Clin Endocrinol Metab*, vol. 89, 2548-2556 (2004).

Khan et al, *Journal of Virology*, vol. 88, No. 21 pp. 12276-12295 (2014).

Kobayashi et al., "Enhancing effects of alpha-, beta-monoglycosylceramides on natural killer cell activity," *bioorganic & Medicinal Chem.*, vol. 4, No. 4, p. 615-619 (1996).

Kodama et al., "c-Jun N-Terminal Kinase Signaling in the Pathogenesis of Nonalcoholic Fatty Liver Disease: Multiple Roles in Multiple Steps," *Hepatology*, vol. 49, pp. 6-8 (2009).

Koziel et al., "Hepatitis C virus (HCV)-specific cytotoxic T lymphocytes recognize epitopes in the core and envelope proteins of HCV," *J. Virol*, Vo. 67, No. 12, pp, 7522-7532 (1993).

Kronenberg et al., Toward an Understanding of NKT Cell Biology: Progress and Paradoxes, *Annu. Rev. Immunol.* vol. 26, pp. 877-900 (2005).

Lalazar et al., "beta-Giycosphingolipids-mediated lipid raft alteration is associated with redistribution of NKT cells and increased intrahepatic COB+ T lymphocyte trapping," *J. Lipid Res*, vol. 49, pp. 1884-1893 (2008).

Lalazar et al., "Modulation of intracellular machinery by beta-glycolipids is associated with alteration of NKT lipid rafts and amelioration of concanavalin-induced hepatitis," *Molecular Immunology*, vol. 45, pp. 3517-3525 (2008).

Lalazar et al., "Glycolipids as Immune Modulatory Tools," *Mini-Reviews in Medicinal Chemistry*, vol. 6, pp. 1249-1253 (2006).

Landgren et al., "Risk of malignant disease among 1525 adult male US veterans with Gaucher disease," *Arch Intern Med*, vol. 167, pp. 1189-1194 (2007).

Liang, *Nature Medicine*, vol. 19, No. 7, pp. 869-878 (2013).

Lippincott, "The Hepatitis C Viruses," *Fields Virology*, vol. 1, pp. 1004-1016 (2001).

Liu et al., JNK: Bridging the insulin signaling and inflammatory pathway, *Current Opinion in Investigational Drugs*, vol. 6, No. 10, pp. 979-987 (2005).

Livovsky et al., Administration of beta-glycolipids overcomes an unfavorable nutritional dependent host milieu: a role 42 for a soy-free diet and natural ligands in intrahepatic COB+ lymphocyte trapping and NKT call redistribution, *International Immunopharmacology*, vol. 8, pp. 1298-1305 (2008).

Luc Van Kaer, a-Galatosylceramide therapy for autoimmune disease: prospects and obstacles, *Nature Revs.* Immunology, vol. 18, No. 7, pp. 31-42 (1997).

Luc Van Kaer, "NKT cells: T lymphocytes with innate effector functions," *Curr. Opin. In Immunology*, vol. 19, pp. 354-364 (2007).

Mackay, et al., "Autoimmune Diseases," *New England Journal of Medicine*, vol. 345, No. 5, pp. 340-350 ((2001).

Major et al., "Hepatitis C Viruses," *Fields Virology*, vol. 1, pp. 1127-1161 (2001).

Makowska et al., "Differences in the Ligans Specificity between CD1d-Restricted T Cells with Limited and Diverse T-Cell Receptor Repertoire," *Scand J. Immunol.*, vol. 52, pp. 71-79 (2000).

Malhi et al., "Molecular Mechanisms of Lipotaxicity in Nonalcoholic Fatty Liver Disease" *Semin Liver Dis*, vol. 28, pp. 360-369 (2008).

Maragoudakis et al., "Effects of thrombin/thrombosis in angiogenesis and tumour progression," *Matrix Biology*, vol. 19, pp, 345-351 (2000).

Matteoni et al., "Nonalcoholic Fatty Liver Disease: A Spectrum of Clinical and Pathological Severity," *Gastroenterology*, vol. 116, pp. 1413-1419 (1999).

Mayeux et al., "Epidemiology of Neurodegeneration," *Annu. Rev. Neurosci.*, vol. 26, pp. 81-104 (2003).

Merck Manual Home Edition, subject "Viral Infections" [online], [Retrieved on Oct. 16, 2008]. Retrieved from the internet: http://www.merck.com/mmhe/print/sec17/ch198/ch198a.html.

Mitsui et al., "Mutations for Gaucher Disease Confer High Susceptibility to Parkinson Disease," *Arch Neural.*, vol. 66, No. 5, pp. 571-576 (2009).

Miyagi et al., Concanavalin A Injection Activates Intrahepatic Innate Immune Cells to Provoke an Antitumor Effect in Murine Liver, *Hepatology*, vol. 40, pp. 1190-1196 (2004).

Miyake et al., "Therapeutic Potential of Glycolipid Ligands for Natural Killer (NK) T Cells in the Suppression of Autoimmune Diseases," *Current Drug Targets-Immune, Endocrine & Metabolic Disorders*; vol. 5, pp, 315-322 (2005).

Miyake et al., NKT Cells and Autoimmune Diseases: Unraveling the Complexity, *Curr. Top. Microbiol. Lmmunol.*, vol. 314, pp. 251-265 (2007).

Mizrahi et al., "beta-Giycoglycosphingolipid-induced augmentation of the anti-HBV immune response is associated with altered COB and NKT lymphocyte distribution: A novel adjuvant for HBV vaccination," *Vaccine*, vol. 26, pp. 2589-2595 (2008).

Motoki et al., "Immunostimulatory and antitumor activities of monoglycosylceramides having various sugar moieties," *boil. Phar. Bull.*, vol. 18, No. 11, pp, 1487-1491 (1995).

Nandi et al., "Biologically active, recombinant DNA in clathyrin-coated vesicles isolated from rat livers after in vivo injection of liposome-encapsulated DNA," *J Biol Chem.*, vol. 261, No. 35, pp. 16722-16726 (1986).

"Neurological disorders" from health-cares.net [online], [retrieved Jan. 6, 2010]. Retrieved from the internet: http://neurology.health-cares.net/>, published online Feb. 7, 2005.

Nicolau et al., "Liposomes as carriers for in vivo gene transfer and expression," *Methods Enzymol.*, vol. 149, pp. 157-176 (1987).

Nicoletti et al., "Murine Concanavalin A-induced hepatitis is prevented by interleukin 12 (IL-12) antibody and exacerbated by exogenous IL-12 through an interferon-gamma-dependent mechanism," *Hepatology*, vol. 32, pp. 728-733 (2000).

Oh et al., "Role of type II NKT cells in the suppression of graft-versus-host disease," *Cril. Rev. Immunol.*, vol. 28, No. 3, pp. 249-267 (2008).

Oki et al., The clinical implication and molecular mechanism of preferentiaiiL-4 production by modified glycolipid-stimulated NKT cells, *J. Clin. Invest.*, vol. 113, pp. 1631-1640 (2004).

Onoe et al., "Th1 or Th2 balance regulated by interaction between dendritic cells and NKT cells," *Immunol Res*, vol. 38, 319-332 (2007).

Ortaldo et al., "Dissociation of NKT Stimulation, Cytokine Induction, and NK Activation In Vivo by the Use of Distinct TCR-Binding Ceramides," *J Immunol*, vol. 172, pp. 943-953 (2004).

Osman et al., "Activation of hepatic NKT cells and subsequent liver injury following administration of alpha-galactosylceramide," *Eur. J. Immunol.*, vol. 30, pp. 1919-1928 (2000).

Porubsky et al., "Normal development and function of invariant natural killer T cells in mice with isoglobotrihexosylceramide (iGb3) deficiency," *PNAS*, vol. 104, No. 14, pp. 5977-5982 (2007).

Racanelli et al., "Presentation of HCV antigens to naïve CD8+T cells: why the where, when, what and how are important for virus control and infection outcome," *Clin Immunol,*, vol. 124, No. 1, pp. 5-12 (2007).

Rollier et al., "Control of Heterologous Hepatitis C Virus Infection in Chimpanzees is Associated with the Quality of Vaccine-Induced Peripheral T-Helper Immune Response," *J. Virol*, vol. 78, No. 1, pp. 187-196 (2004).

(56) References Cited

OTHER PUBLICATIONS

Rouhl, A.M., "Metabolic Syndrome," *Chemical & Engineering News*, vol. 82, No. 47, pp. 83-99 (2004).
Sandberg et al., "Development and function of CD1d-restricted NKT cells: influence of sphingolipids, SAP and sex," *Trends in Immunology*, vol. 26, pp. 347-349 (2005).
Selkoe et al., "Alzheimer's disease: Genes, proteins, and therapy," *Physiol. Rev.*, vol. 81, No. 2, pp. 741-766 (2001).
Shevach Ethan, "From vanilla to 28 flavors: Multiple varieties of T regulatory cells," *Immunity*, vol. 25, pp. 195-201 (2006).
Singh et al., "Natural Killer T Cell Activation Protects Mice Against Experimental Autoimmune Encephalomyelitis," *J. Exp. Med.*, vol. 194, No. 12, pp. 1801-1811 (2001).
Singh et al., "Differential Effects of JNK1 and JNK2 Inhibition on Murine Steatohepatitis and Insulin Resistance," Hepatology, vol. 49, pp. 87-96 (2009).
Skold et al, "Role of CD1d-Restricted NKT Cells in Microbial Immunity," *Infection and Immunity*, vol. 71, No. 10, pp. 5447-5455 (2003).
Slife et al., "Free sphingosine formation from endogenous substrates by a liver plasma membrane system with a divalent cation dependence and a neutral pH optimum," *J Biol. Chem.*, vol. 264, No. 18, pp. 10371-10377 (1989).
Smith et al., "Traditional sampling with laboratory analysis and solid phase microextraction sampling with field gas chromatography/mass spectrometry by military industrial hygienists," *AIHA Journal*, vol. 63, pp. 284-292 (2002).
Smyth et al.,, *Current Opinion in Immunology*, vol. 14, pp. 165-171 (2002).
Stanic et al., "Another View of T Cell Antigen Recognition: Cooperative Engagement of Glycolipid Antigens by Va14Ja18 Natural TCR," *The Journal of Immunology*, vol. 171, pp. 171-184 (2003).
Stanic et al., Innate self recognition by an invariant, rearranged T-cell receptor and its immune consequences, *Immunology*, vol. 109, pp. 4539-4551 (2003).
Stevenson et al., "The epidemiology of influenza," *Occup. Med.*, vol. 52, (2002)—Abstract Only.
Summers, et al., "A Role for Sphingolipids in Producing the Common Features of Type 2 Diabetes, Metabolic Syndrome X, and Cushing's Syndrome," *Diabetes*, vol. 54. pp. 591-602 (2005).
Sweeley, "Glycosphingolipids: structure and function," *Pure & Appl. Chem.*, vol. 61, No. 7, pp. 1307-1312 (1989).
Takeda et al., *Human Cell*, vol. 14, No. 3, pp. 159-163 (2001).
Takeda et al., "Critical contribution of liver natural killer T cells to a murine model of hepatitis," *PNAS*, vol. 97, No. 10. pp. 5498-5503 (2000).
Tan et al., "Strategies for hepatitis C therapeutic intervention: now and next," *curr. Opin in Pharmacology*, vol. 4, pp. 465-470 (2004).
Taniguchi et al., "The regulatory role og Valpha14 NKT cells in innate and acquired immune response," *Annu. Rev. Immunol.*, vol. 21, pp. 483-513 (2003).
Tessmer et al., "NKT cell immune responses to viral infection," *Expert Opin. Ther. Targets*, vol. 13, No. 2, pp. 153-162 (2009).
Tiegs et al., "Cellular and Cytokine-Mediated Mechanisms of Inflammation and its Modulation in Immune-Mediated Liver Injury," *Gastroenterol*, vol. 45, pp. 63-70 (2007).
Todar, K., "Bacterial Resistance to Antibiotics," in Todar's Online Textbook of Bacteriology [online], [Retrieved on Dec. 28, 2008]. Retrieved from the internet: http://www.textbookofbacteriology.net/resantimicrobial.html, pp. 1-4.
Tomura et al., "A Novel Function of Valpha14+CD4+NKT Cells: Stimulation of IL-12 Production by Antigen-Presenting Cells in the Innate Immune System," *J Immunol*, vol. 163, pp. 93-101 (1999).
Torisu et al., Suppressor of Cytokine Signaling 1 Protects Mice Against Concanavalin A-Induced Hepatitis by Inhibiting Apoptosis, *Hepatology*, vol. 47, pp. 1644-1654 (2008).
Trayhurn et al., "Adipose Tissue and Adipokines—Energy Regulation from the Human Perspective," *J. Nutr.*, vol. 136, pp. 1935S-1939S (2006).
Trinchera et al., "Recycling of glucosyleramide and sphingosine for the biosynthesis of gangliosides and sphingomyelin in rat liver," *Biochem J.*, vol. 270, No. 3, pp. 815-820 (1990).
Tsuji et al., "Glycolipids and phospholipids as natural CD1d-binding NKT cell ligands," *Cell. Mol. Life Sci.*, vol. 63, pp. 1889-1898 (2006).
Tupin et al., "The unique role of natural killer T cells in the response to microorganisms," *Nature Rev. Microbiology*, vol. 5, pp. 405-417 (2007).
Uemura et al., "Role of human non-invariant NKT lymphocytes in the maintenance of type 2 T helper environment during pregnancy," *International Immunology*, vol. 20, No. 3, pp. 405-412 (2008).
Van der Vliet et al., Immunology, vol. 98, pp. 557-563 (1999).
Vanderkerken et al., "The 5T2MM murine model of multiple myeloma," *Methods in Mol. Med.*, vol. 113, pp. 191-205 (2005).
Weisberg et al. "Obesity is associated with macrophage accumulation in adipose tissue," *J. Clin. Invest.*, vol. 112, pp. 1796-1808 (2003).
Wilson et al., "Natural Killer T Cells as Targets for Therapeutic Intervention in Autoimmune Diseases," *Current Pharmaceutical Design*, vol. 9, pp. 201-220 (2003).
Xu et al., "Chronic inflammation in fat plays a crucial role in the development of obesity-related insulin resistance," *J. Clin. Invest.*, vol. 112, pp. 1821-1830 (2003).
Yamamura et al., "NKT Cell-Stimulating Synthetic Glycolipids as Potential Therapeutics for Autoimmune Disease," *Current Topics in Medicinal Chemistry*, vol. 4, pp. 561-657 (2004).
Yang et al., "Role of Interferon-y in GVHD and GVL," *Cellular & Molecular Immunology*, vol. 2, No. 5, pp. 323-329 (2005).
Yu et al., "Production and characterization of monoclonal antibodies against complexes of the NKT cell ligand a-galactosylceramide bound to mouse CD1d," *Journal of Immunological Methods*, vol. 32, pp. 11-23 (2007).
Yu et al., "Modulation of CD1d-restricted NKT cell responses by using N-acyl variants of alpha-galactosylceramides," *PNAS*, vol. 102, No. 9, pp. 3383-3388 (2005).
Zajonc et al., "Structure and function of a potent agonist for the semi-invariant natural killer T cell receptor," *Nature Immunology*, vol. 6, No. 8, pp. 810-818 (2005).
Zhou et al., "The Immunological Function of iGb3," *Current Protein and Peptide Science*, vol. 7, pp. 325-333 (2006).
Zigmund et al., "Treatment of non-alcoholic steatohepatitis by beta-glucoceramide: A phase 1/11 clinical study," *Hepatology*, vol. 44, pp. 180A (2006).
Zigmund et al., "beta-Giucosylceramide: a novel method for enhancement of natural killer T lymphoycte plasticity in murine models of immune-mediated disorders," *Gut*, vol. 56, pp. 82-89 (2007).
Zigmund et al., "beta-Giycosphingolipids improve glucose intolerance and hepatic steatosis of the Cohen diabetic rat," *Am J Physiol Endocrinol Metab*, vol. 296, pp. E72-E78 (2009).
Zitzmann et al., "Abnormal Glycosylation in Disease and Therapy: Relevance to Chronic Viral Infections," The Glycobiology Institute, Dept. of Biochemistry, Oxfor University, Oxford, United Kingdom; Viral Hepatitis Group, Kimmel Cancer Center, Jefferson Medical College, Philadelphia, Pennsylvania, USA, 1999 (Abstract only).
Baldwin et al., "Do NSAIDs contribute to acute fatty liver of pregnancy?," *Medical Hypotheses*, vol. 54, No. 5, pp. 846-849 (2000).
Kaneda et al., "Inflammatory Liver Steatosis Caused by IL-12 and IL-18," *Journal of Interferon & Cytokine Research*, vol. 23, pp. 155-162 (2003).
Saygan-Karamürsel et al., "Acute fatty liver of pregnancy after aspirin intake," *J. Matern. Fetal Neonatal Med.*, vol. 16, No. 1, pp. 65-66 (2004).
Ishihara et al., "α-Glycosylceramides Enhance the Antitumor Cytotoxicity of Hepatic Lymphocytes Obtained from Cancer Patients by Activating CD3$^-$CD56$^+$NK Cells In Vitro," *The Hournal of Immunology*, vol. 165, pp. 1659-1664 (2000).
Motoki et al., "Antitumor Activities of α-, β-Monogalactysylceramides and Four Diastereomers of an α-Galactosylceramide," *Bioorganic & Medicinal Chemistry Letters*, vol. 5, No. 7, pp. 705-170 (1995).

(56) References Cited

OTHER PUBLICATIONS

Buczko et al., "Aspirin and the fibrinolytic response," *Thrombosis Research*, vol. 110, pp. 331-334 (2003).
Di Micco et al., "Anti-thrombin action of low-dose acetylsalicylic acid," *European Journal of Pharmacology*, vol. 460, pp. 59-62 (2003).
Ramalho, Fernando, "Hepatitis C virus infection and liver steatosis," *Antiviral Research*, vol. 60, pp. 125-127 (2003).
Szczeklik et al., "Aspirin and thrombinogenesis," *Thrombosis Research*, vol. 110, pp. 345-347 (2003).
Zeller et al., "Influence of Valproate Monotherapy on Platelet Activation and Hematologic Values," *Epilepsia*, vol. 40, No. 2, pp. 186-189 (2009).
"Non-alcoholic fatty liver disease," Wikipedia, Aug. 9, 2016.
Adar and Ilan, "beta-Glycosphingolipids as immune modulators," *J Immunotoxicol.*, vol. 5, No. 2, pp. 209-220 (2008).
Long et al., "Characterization of human immunodeficiency virus type 1 gp120 binding to liposomes containing galactosylceramide," *J. Virol.*, vol. 68, No. 9, pp. 5890-5898 (1994).
Feffer et al., "Thrombotic tendencies and correlation with clinical status in patients infected with HIV," *South Med. J.*, vol. 88, No. 11, pp. 1126-1130 (abstract only) (1995).
Gomez-Reino et al., "Inflammation and HIV infection: a friendly connection," *Lancet*, vol. 348, Suppl. II, p. 24 (1996).

\* cited by examiner

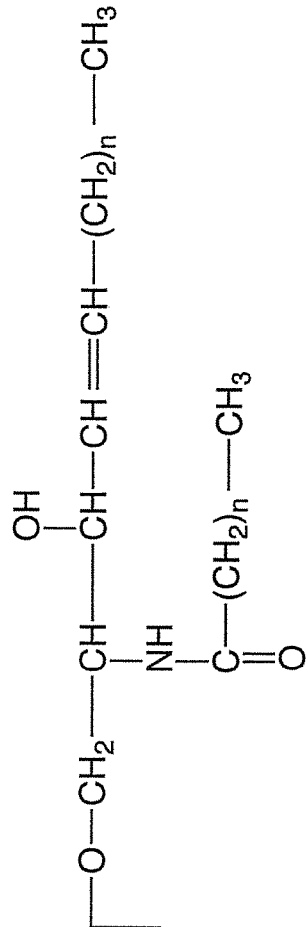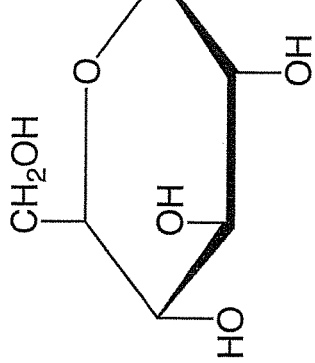
Figure 1

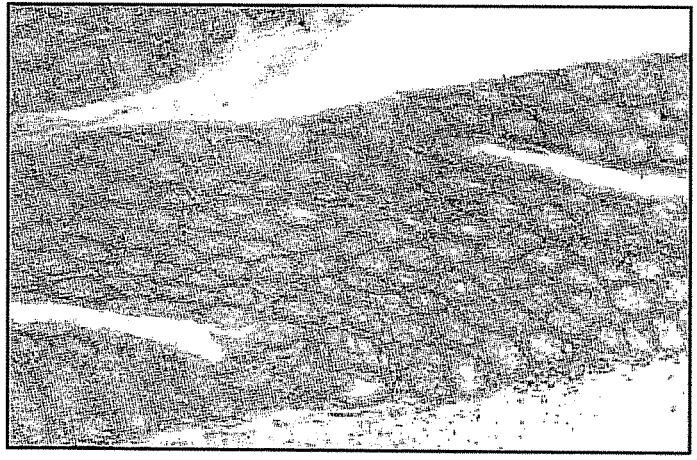
GC TREATED
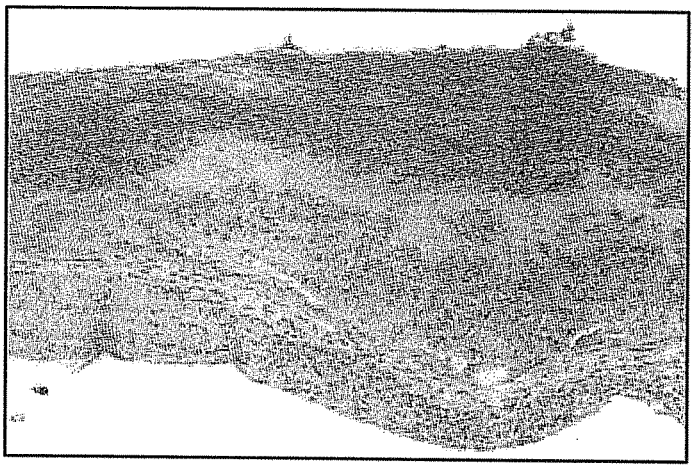
CONTROL
FIG. 13

GLUCOCEREBROSIDE TREATMENT OF DISEASE

REFERENCE TO RELATED PATENT APPLICATIONS

This application is a continuation-in-part of U.S. patent application Ser. No. 10/375,906, filed on Feb. 27, 2003, entitled "Regulation of Immune Responses by Manipulation of Intermediary Metabolite Levels." The content of the aforementioned patent application is hereby incorporated by reference, in its entirety.

FIELD OF THE INVENTION

This invention relates to the use of a naturally occurring, mammalian intermediary metabolite or T cell receptor ligand, preferably Glucocerebroside, for the treatment of immune mediated or immune related diseases or disorders, infectious diseases, metabolic disorders and cancer in mammalian subjects.

All patents, patent applications, patent publications, scientific articles, and the like, are hereby incorporated by reference in their entirety in order to describe more fully the state of the art to which the present invention pertains.

BACKGROUND OF THE INVENTION

Various methods have been described for the treatment of immune-related or immune mediated disorders or diseases, infectious diseases, metabolic disorders and different types of cancer in mammalian subjects. One of these methods involves the modulation of immune responses in a subject. This includes the down regulation of the immune response system using procedures or combinations of procedures for producing and applying a new and unexpected immune modulation termed selective immune down regulation (SIDR). Immunological modulation is an artificially induced variation in a subject's immune system in response to the introduction of reagents, procedures and processes. These procedures have been described in detail in U.S. patent application Ser. No. 08/808,629, filed on Feb. 28, 1997, U.S. patent application Ser. No. 10/377,628, filed on Mar. 4, 2003, U.S. application Ser. No. 10/377,603, filed on Mar. 4, 2003, U.S. patent application Ser. No. 09/447,704, filed on Feb. 28, 1997, U.S. application Ser. No. 10/385,440, filed on May 9, 2001, and U.S. application Ser. No. 09/356,294, filed on Jul. 16, 1999. Each if the foregoing patents are incorporated by reference in their entirety in the present application and may further be used in conjunction with the present invention.

Other methods describe the use of educated or treated cells in the treatment of a variety of diseases. Specifically, the methods are directed to the manipulation of the NKT cell population in a subject that results in the modulation of the Th1/Th2 balance toward anti-inflammatory or pro-inflammatory cytokine producing cells. A detailed description of these inventions have been disclosed in U.S. Patent Application entitled "Educated NKT Cells and Their-Uses in the Treatment of Immune-Related Disorders" by Yaron Ilan et al., filed on Jun. 25, 2003 (Application No. not yet assigned), PCT Application No. IL01/01197, filed on Dec. 24, 2001, and U.S. application Ser. No. 10/375,906, filed on Feb. 27, 2003. Each of the foregoing patents is incorporated by reference in its entirety in the present application and may further be used in conjunction with the present invention.

The present invention provides a new method for the treatment of immune-related or immune mediated disorders or diseases, infectious diseases, metabolic disorders and different types of cancer in mammalian subjects, and preferably, human subjects. This method involves the administration of an intermediary metabolite or a T cell receptor ligand to a subject. Other methods disclosed herein use this administration step along with other procedures described in prior patent applications incorporated by reference herein. These methods are further described in detail below.

An intermediary metabolite or a T cell receptor ligand is used in the present invention for the treatment of disease. The intermediary metabolite or the T cell receptor ligand may comprise a lipid or conjugated biomolecule. The conjugated biomolecule may in turn comprise a glycolipid, lipoprotein, apolipoprotein, or glycoprotein other than antibodies, cytokines, or hormones. A glycolipid may comprise a monosaccharide ceramide. A monosaccharide ceramide may comprise a glucosylceramide or galactosylceramide.

Glucosylceramide is a naturally occurring glycolipid consisting of ceramide, to which glucose is attached. A ceramide, which is a sphingosine and a fatty acid, is the structural unit common to all sphingolipids. Sphingolipids have a variety of cellular functions. These include membrane structural roles and cell signaling participation. (Sullard et al., 2000 Journal of Mass Spectrometry 35: 347-353.) Glucosylceramide is made by the enzyme glucosylceramide synthase which attaches the two molecules together. (see FIG. 1 and FIG. 2). An example of a glucosylceramide includes glucocerebroside, or a glucocerebroside analogue or derivative.

The genetic disease Gaucher's Disease is characterized by an accumulation of glucosylceramide. In the treatment of this disorder by appropriate enzyme therapy, the excess glucosylceramide is degraded. Two side effects of this treatment have been noted. In the course of this treatment, chronic active hepatitis associated with Hepatitis C virus infection was exacerbated. Additionally, certain patients (with pre-diabetic conditions) experienced the development of diabetic conditions, indicating an onset of Type II Diabetes. These observations further directly confirm that in human subjects, Glucosylceramide levels regulate the onset of immune-mediated or immune-regulated disorders or diseases.

SUMMARY OF THE INVENTION

This invention relates to the use of a naturally occurring, mammalian intermediary metabolite or T cell receptor ligand, for the treatment of immune mediated or immune related diseases or disorders, infectious diseases, metabolic disorders and cancer in mammalian subjects. In a preferred embodiment, such mammalian subjects are human beings.

This invention provides a process for treating a disease in a mammalian subject comprising administering to the subject an effective amount of a mammalian intermediary metabolite.

This invention further provides a process for treating a disease in a mammalian subject comprising administering to said subject an effective amount of a T cell receptor ligand.

The present invention also provides a process for treating a disease in a mammalian subject comprising administering to said subject an effective amount of Glucocerebroside.

Another aspect of the present invention provides for the treatment of a disease in a mammalian subject comprising the ex vivo treating or educating of cells obtained from the mammalian subject. The cells are treated or educated with an effective amount of the intermediary metabolite.

The treated or educated cells are then re-administered to the subject.

Another aspect of the present invention provides for the treatment of a disease in a mammalian subject comprising the ex vivo treating or educating of cells obtained from the mammalian subject. The cells are treated or educated with an effective amount of the T cell receptor ligand. The treated or educated cells are then re-administered to the subject.

Yet another aspect of the present invention provides for the treatment of a disease in a mammalian subject comprising the ex vivo treating or educating of cells obtained from the mammalian subject. The cells are treated or educated with an effective amount of Glucocerebroside. The treated or educated cells are then re-administered to the subject.

The present invention also relates to the treatment of a disease in a mammalian subject comprising the re-administration of treated or educated cells to the subject, and the direct administration to said subject of an effective amount of intermediary metabolite.

The present invention provides for the treatment of a disease in a mammalian subject comprising the re-administration of treated or educated cells to the subject, and the direct administration to said subject of an effective amount of T cell receptor ligand.

The present invention also relates to the treatment of a disease in a mammalian subject comprising the re-administration of treated or educated cells to the subject, and the direct administration to said subject of an effective amount of Glucocerebroside.

Numerous other aspects and embodiments of the present invention are described in further detail below.

BRIEF DESCRIPTION OF THE FIGURES

FIG. 1 shows the chemical structure of Glucocerebroside.

FIG. 13 shows colonic histological sections prepared from mice.

DETAILED DESCRIPTION OF THE INVENTION

Figure 2:
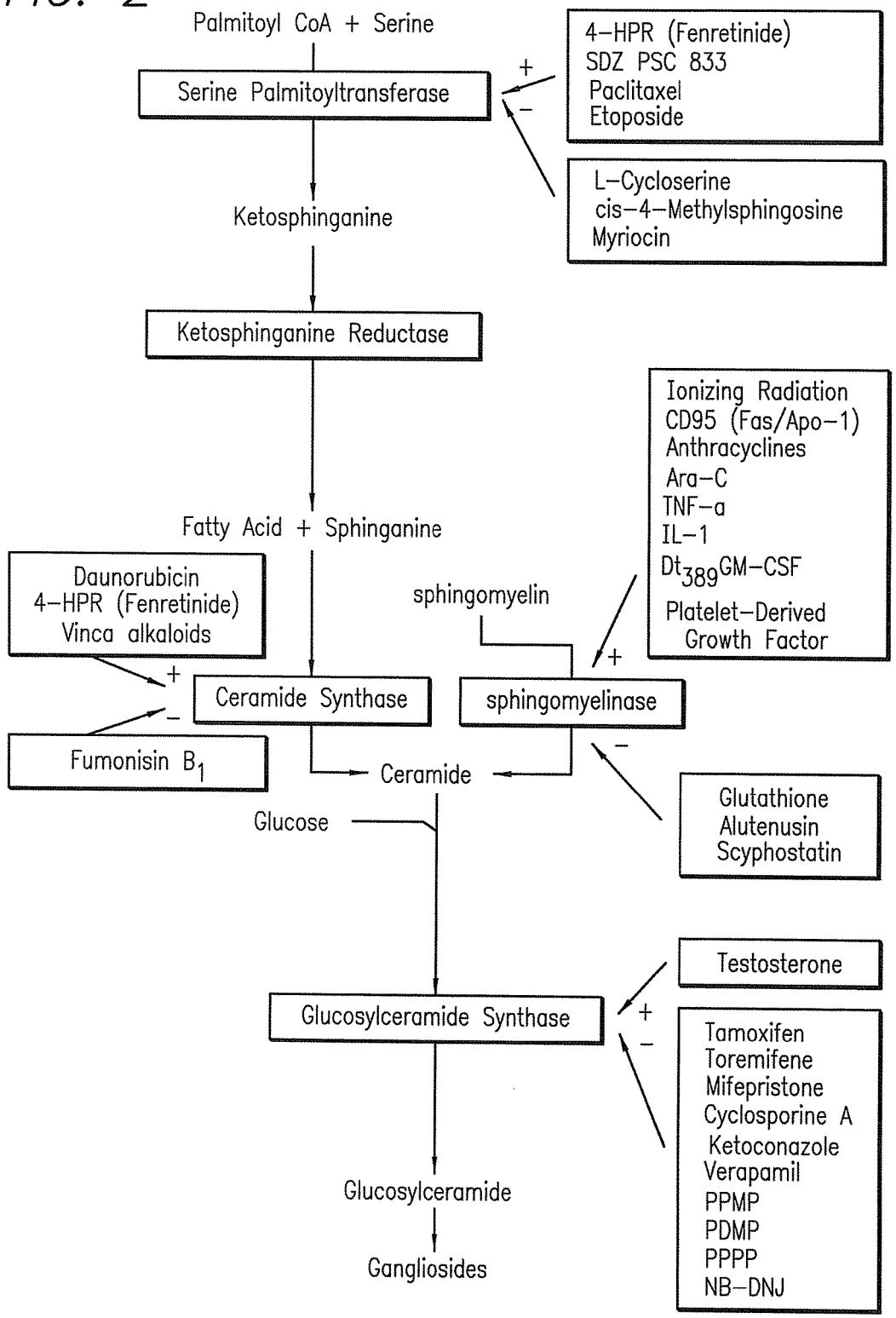
FIG. 2 shows the pathway to Glucosylceramide synthesis.

The present invention provides methods for the treatment of a disease in a mammalian subject by the administration of an effective amount of an intermediary metabolite to the subject. The intermediary metabolite includes, but is not limited to a T cell receptor ligand, a lipid, a polar lipid, a conjugated biomolecule, a glycolipid, a lipoprotein, an apolipoprotein, a glycoprotein, a monosaccharide or polysaccharide ceramide, a glucosylceramide, a galactosylceramide, a glucocerebroside, a glucocerebroside analogue or derivative, a sphingosine, a sphingolipid or a ceramide. In a preferred embodiment of the invention, the mammalian subject is a human being.

The present invention describes a method for treating a disease where regulatory, immune-regulatory or NKT cells are obtained from the subject to be treated, or from another subject, and are educated or treated ex vivo. The cells are treated or educated by the presence of intermediary metabolite, antigens or epitopes, and antigen presenting cells, or any combination thereof. The treated or educated cells are then re-administered to the subject. The cells may be administered to the subject by adoptive transfer.

In addition to the method described above involving the ex vivo treatment or education of cells, the present invention also provides for a method where the ex vivo treatment or education is accompanied by the method of directly administering to the subject to be treated, by a variety of ways, an effective amount of the intermediary metabolite, antigen presenting cells, and antigens or epitopes, or any combination of the above. The disease may also be treated by only the direct administration of an effective amount of the intermediary metabolite, antigen presenting cells, and antigens or epitopes, or any combination of the above.

A therapeutic composition for the use in the treatment of the disease may comprise an effective amount of the intermediary metabolite, antigen presenting cells, and antigens or epitopes, or any combination of the above.

The treatment of a disease in any of the described methods results in a change in the number or function of regulatory, immune-regulatory or NKT cells. This change encompasses a reduction, inhibition, or decrease in the number or function of the cells. This inhibition may be caused by the competitive displacement of activating elements from the CD1d molecule. A change may also include a stimulation or increase in the number or function of the cells. This stimulation may be caused by increased binding of the activating elements from the CD1d molecule.

The treatment of a disease may also result in a change the cytokine responses. Any cytokine in the immune system may be involved in these responses. The change could result in a pro-inflammatory or an anti-inflammatory response. There may also be a pro-inflammatory, and an anti-inflammatory response since certain cytokines may increase and others may decrease, simultaneously.

Another result of the treatment of a disease is an alteration of the regulatory, immune-regulatory or NKT cell distribution in the subject. This change may also be accompanied by a change in the peripheral/intrahepatic T cell ratio. A further result may also include a change in intrahepatic CD8+ T cell trapping. There may be an increase or a decrease in the intrahepatic trapping. The result may also include a change in intrasplenic T cell trapping, where said change could be an increase or decrease.

Also provided in the present invention are two in vitro screening assays for an analogue or derivative of an intermediary metabolite which is administered to the subject to treat a disease. The first assay involves providing regulatory, immune-regulatory or NKT cells from the subject being treated or another subject, antigen presenting cells, and an analogue or derivative of the intermediary metabolite in vitro. If a decrease in the regulatory, immune-regulatory or NKT cell proliferation is identified, then that specific analogue or derivative is a treatment for disease.

The second assay involves providing in a first test tube, regulatory, immune-regulatory or NKT cells and BSA; in a second test tube, regulatory, immune-regulatory or NKT cells and the analogue or derivative of an intermediary metabolite; in a third test tube, regulatory, immune-regulatory or NKT cells, antigen presenting cells and BSA; and in a fourth test tube, regulatory, immune-regulatory or NKT cells, antigen presenting cells and the analogue or derivative of the intermediary metabolite. If the least amount of regulatory, immune-regulatory or NKT cell proliferation is found in the fourth test tube, then that specific analogue or derivative is a treatment for the disease.

In a preferred embodiment of the present invention, there is minimal interference with digestion and absorption of an intermediary metabolite, an analogue or derivative of an intermediary metabolite, a lipid, conjugated biomolecule, polar lipid, glycolipid, lipoprotein, apolipoprotein, cytokines or hormones, monosaccharide ceramide, glucosylceramide, galactosylceramide; glucocereboside, glucocereboside analogue or derivative, sphingosine, sphingolipid, ceramide, T cell ligand, T cell receptor ligand, a T cell receptor ligand analogue or derivative, or a glycoprotein other than an antibody, in the mammalian subject. Specifically, the mammalian subject has been without food and/or water for a certain amount of hours prior to the administration of the aforesaid molecules, treatment of the mammalian subject or the manipulation of cells in the mammalian subject.

The methods for carrying out the invention, and the experimental results which support and further explain the results obtained are as follows:

EXAMPLES

I. Glucocerebroside Treatment of Concanavalin-A Hepatitis

Materials and Methods
Reagents

Concanavalin A was purchased from Worthington biochemical corporation, USA.

Glucocerebroside (Glucosylceramide or Glucosylcerebroside) was purchased from Avanti Polar Lipids, Inc.
Animals Five groups of male Balb/C mice (n=6/group) were studied.
Serum Transaminase Measurement Serum ALT and AST plasma activity were measured by an automated commercial kit (Kodak SMA).

Hepatic Histology Examination

Histological sections of the livers from all mice were examined to determine the degree of liver damage. For each mouse a single liver segment was fixed in 10% buffered formaldehyde and embedded in paraffin for histologic analysis. Sections were stained with hematoxylin/eosin and histologic evaluation was performed.
Measurement of Cytokine Levels Blood was drawn from mice in all groups and centrifuged at 14,000 rpm. Serum IFNγ, IL2, IL4, IL10 and IL-12 levels were measured by "sandwich" ELISA using Genzyme Diagnostics kits (Genzyme Diagnostics, Mass.).
Splenic and Hepatic Lymphocyte Isolation Splenocytes were isolated and red blood cells removed as previously described [Vicari, A. P., et al., Immunology Today 17(2):71 (1996)]. Intrahepatic lymphocytes were isolated from all groups of mice at the end of the study, as previously described, with some modifications [Vicari et al., (1996) ibid.; Bleicher, P. A., et al., Science 250:679-682 (1990)]. The inferior vena cava was cut above the diaphragm and the liver was flushed with 5 ml of cold PBS until it became pale. The connective tissue and the gall bladder were removed, and livers were place in a 10-ml dish in cold sterile PBS. Livers and spleens were crushed through a stainless mesh (size 60, Sigma Chemical Co., St. Louis Mo.). Cell suspension was placed in a 50 ml tube for 3 minutes and washed twice in cold PBS (1,250×rpm for 10 minutes), and debris was removed. Cells were resuspended in PBS, cell suspension was placed through a nylon mesh presoaked in PBS, and unbound cells were collected. Cells were washed twice in 45 ml PBS (1,250×rpm in room temperature). For liver and spleen lymphocyte isolation 20 ml of histopague 1077 (Sigma Diagnostics, St. Louis, Mo.) were slowly placed underneath the cells suspended in 7 ml of PBS, in a 50-ml tube. The tube was centrifuged at 1,640 rpm for 15 minutes at room temperature. Cells at the interface were collected, diluted in a 50-ml tube, and washed twice with ice-cold PBS (1,250 rpm for 10 minutes). Approximately $1 \times 10^6$ cells/mouse liver were recovered. The viability by trypan blue staining was more than 95%. Both splenocytes and liver-associated lymphocytes were isolated from all animals in all experimental groups.
Flow Cytometry Analysis for NKT Lymphocytes in Peripheral Blood Immediately following intrahepatic and intrasplenic lymphocyte isolation, triplicates of $2-5 \times 10^4$ cells/500 µl PBS were put into Falcon 2052 tubes incubated with 4 ml of 1% BSA for 10 minutes, and centrifuged at 1400 rpm for 5 minutes. Cells were resuspended in 10 µl FCS with anti-NK1.1 and anti-CD3 antibodies (Pharmingen, USA) and mixed every 10 minutes for 30 minutes. Cells were washed twice in 1% BSA, and kept in 4° C. until reading. For the control group, only 5 µl of 1% BSA was added. Analytical cell sorting was performed on $1 \times 10^4$ cells from each group with a fluorescence-activated cell sorter (FACSTAR plus, Becton Dickinson). Only live cells were counted, and background fluorescence from non-antibody-treated lymphocytes were deducted from the levels obtained. Gates were set on forward- and side-scatters to exclude dead cells and red blood cells. The data were analyzed with Consort 30 two-color contour plot program (Becton Dickinson, Oxnard, Calif.), or the CELLQuest program.

Example 1

Glucocerebroside Amelioration of Concanavalin-A Hepatitis by the Inhibition of NKT Regulatory Lymphocytes To evaluate the immune modulatory effect of Glucocerebroside on Concanavalin-A (Con-A) induced hepatitis, five groups of Balb/C mice, consisting of 6 mice each were studied. Group A and Group B were treated intraperitoneally with 1 µg Glucocerebroside two hours prior to and two hours following, respectively, the intravenous administration of 500 µg of Con-A. Group C mice received only 500 µg of Con-A, and no Glucocerebroside. Group D mice were treated with 1 µg Glucocerebroside, and no Con-A. Group E mice were naïve controls. This is summarized in Table 1.

TABLE 1

Experimental and Control Groups

| Group | ConA (IV 500 ug) | Glucocerebroside (IP 1 ug) |
|---|---|---|
| A | + | +(2 hours before ConA) |
| B | + | +(2 hours after ConA) |
| C | + | − |
| D | − | + |
| E | − | − |

Figure 3:
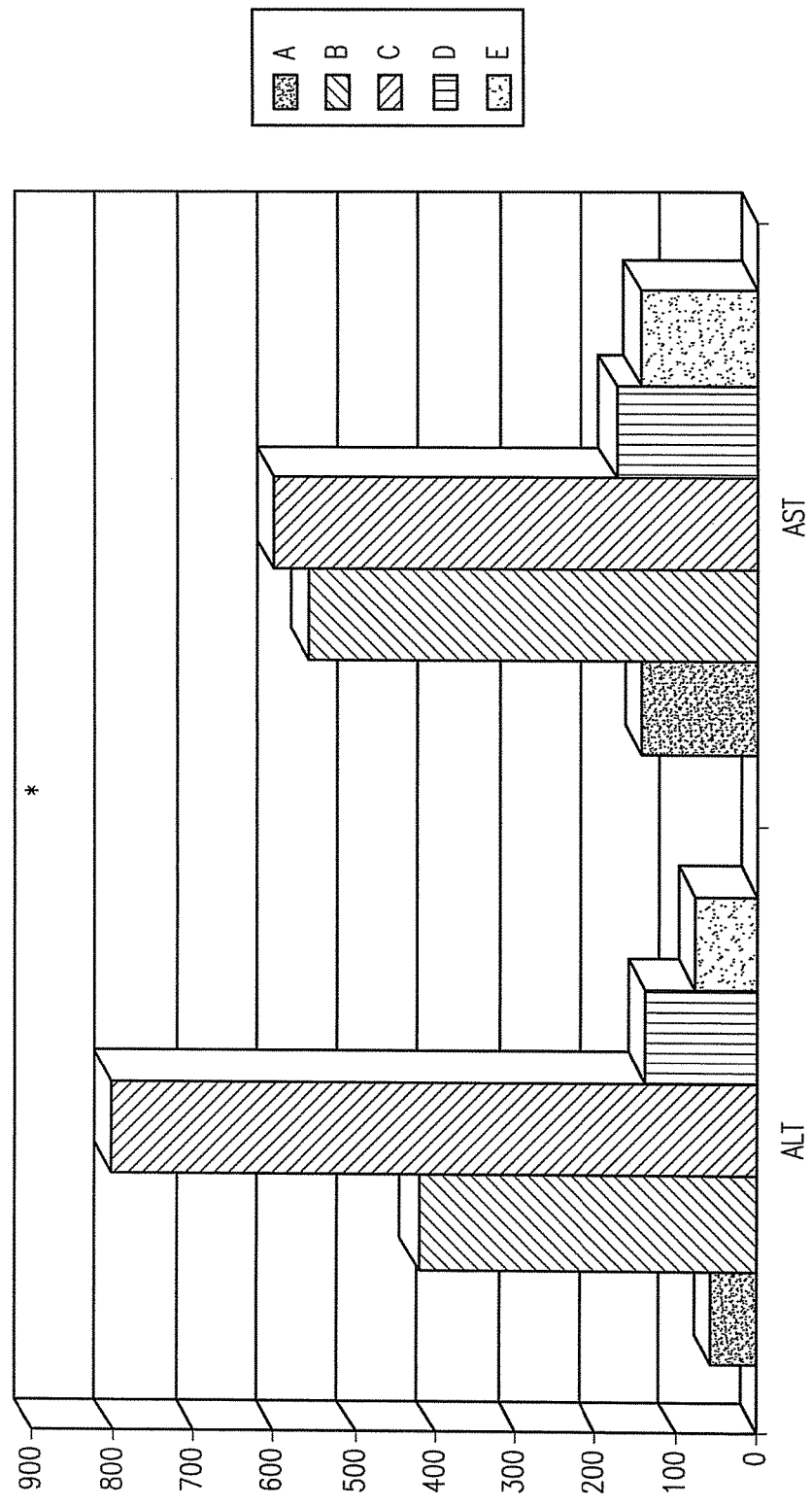
FIG. 3 shows the effect of Glucocerebroside on liver enzymes.

Treatment with Glucocerebroside significantly ameliorated Con-A induced hepatitis, as shown in FIG. 3 by markedly reduced serum AST and ALT levels. Group A had an ALT level of 57 IU. Group B and Group C had ALT levels of 420 IU and 801 IU, respectively. Group A had an AST level of 143 IU. Group B and Group C had AST levels of 559 IU and 600 IU, respectively. The administration of Glucocerebroside alone in Group D did not show a significant change in AST or ALT levels compared to Group E, the naïve control.

Figure 4:
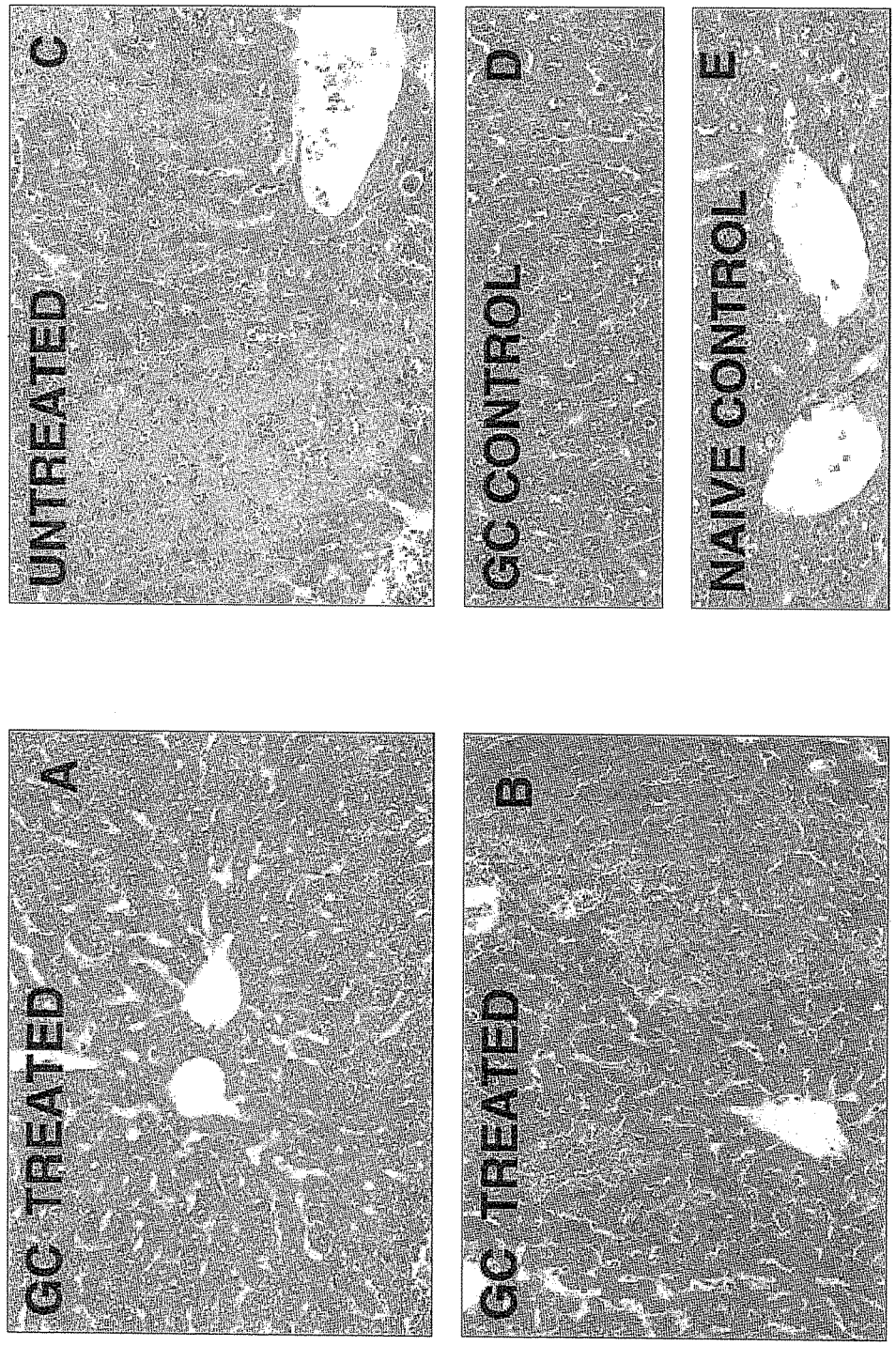
FIG. 4 shows liver histological sections prepared from mice.

As shown in Table 2, treatment with Glucocerebroside two hours before Con-A administration in Group A resulted in normal results in almost all biopsies. Group B and Group C mice showed ischemia, necrosis and apoptosis. As shown in FIG. 4, liver histological sections prepared from Group A and Group B mice revealed markedly attenuated damage compared to sections prepared from Group C livers, in which massive hepatocyte damage and characteristic apoptosis related changes were present.

TABLE 2

Effect of Glucocerebroside on Liver Pathology

| A | Normal in almost all biopsies |
|---|---|
| B | Ischemia, necrosis, apoptosis |
| C | Ischemia, necrosis, apoptosis |
| D | Normal |
| E | Normal |

Figure 5:
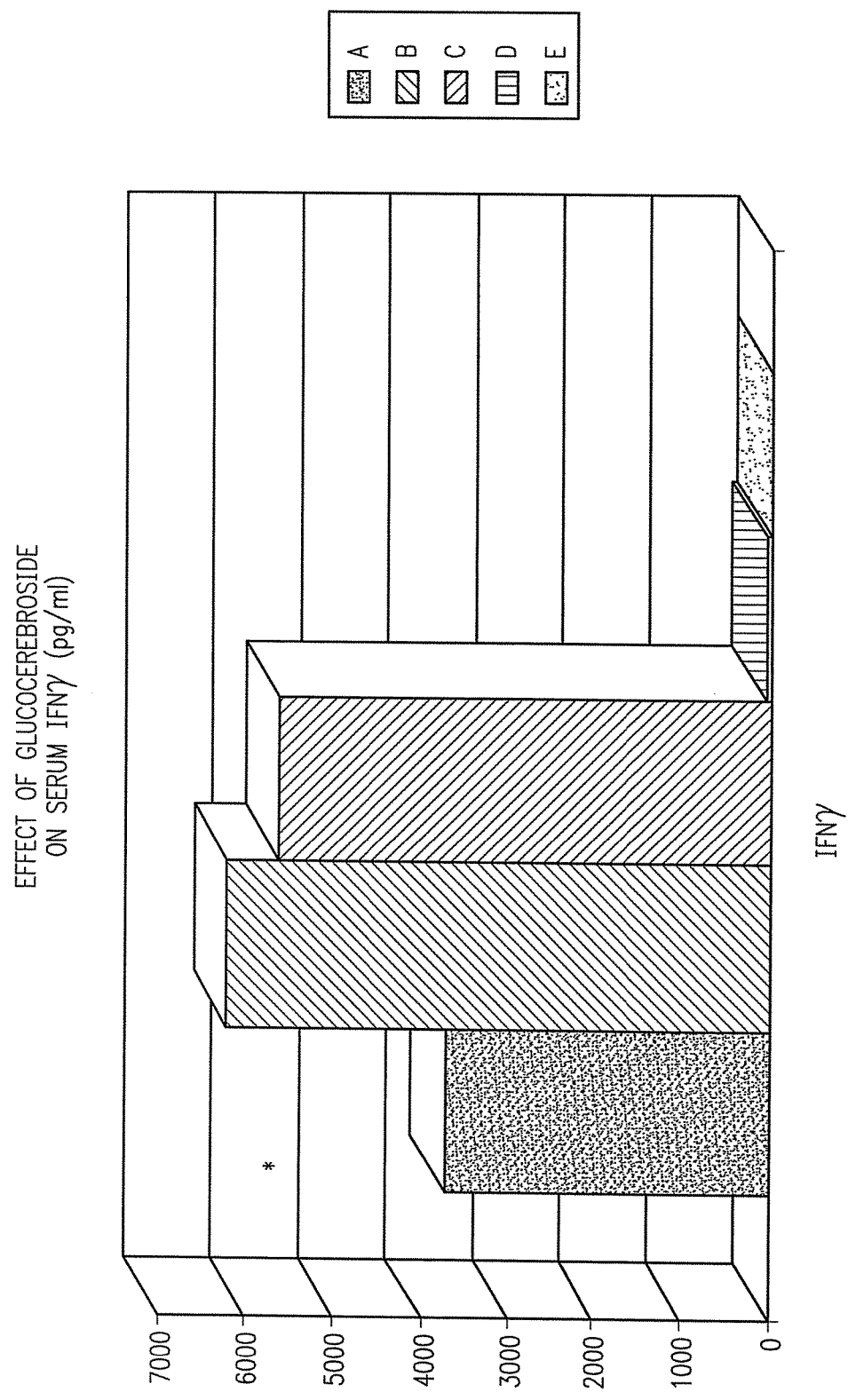
FIG. 5 shows the effect of Glucocerebroside on Serum IFNγ.
Figure 6:
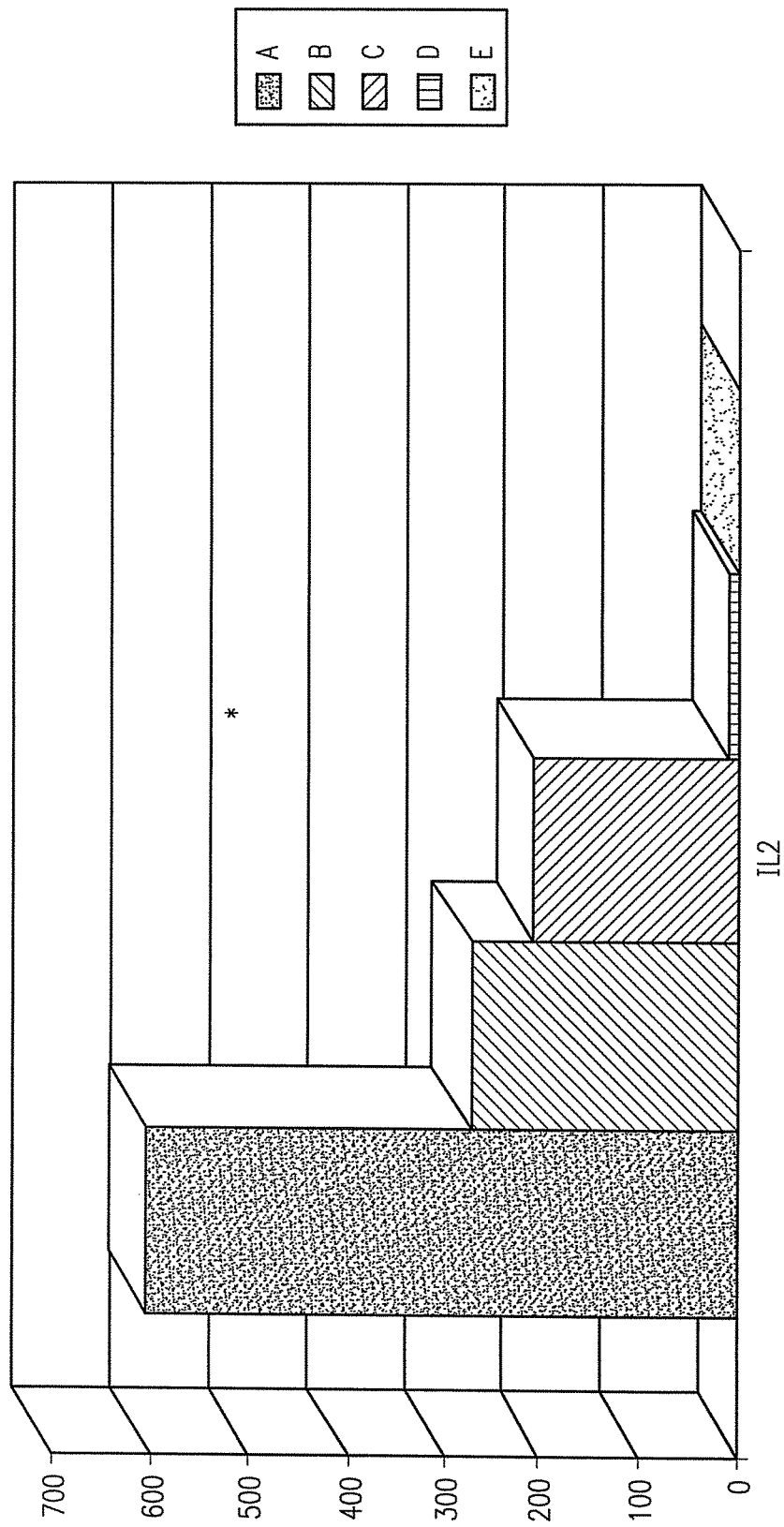
FIG. 6 shows the effect of Glucocerebroside on Serum IL2.
Figure 7:
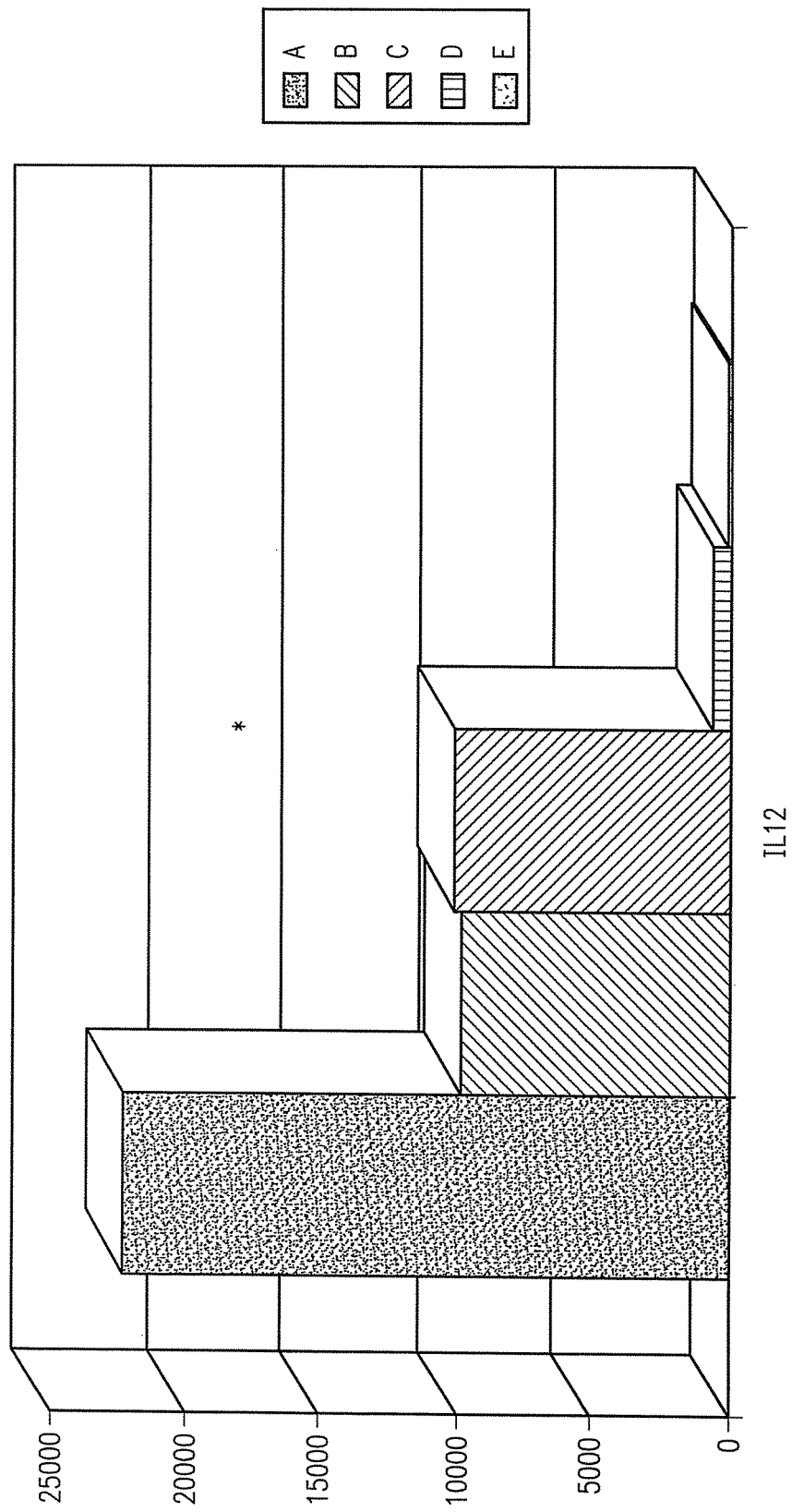
FIG. 7 shows the effect of Glucocerebroside on Serum IL12.
Figure 8:
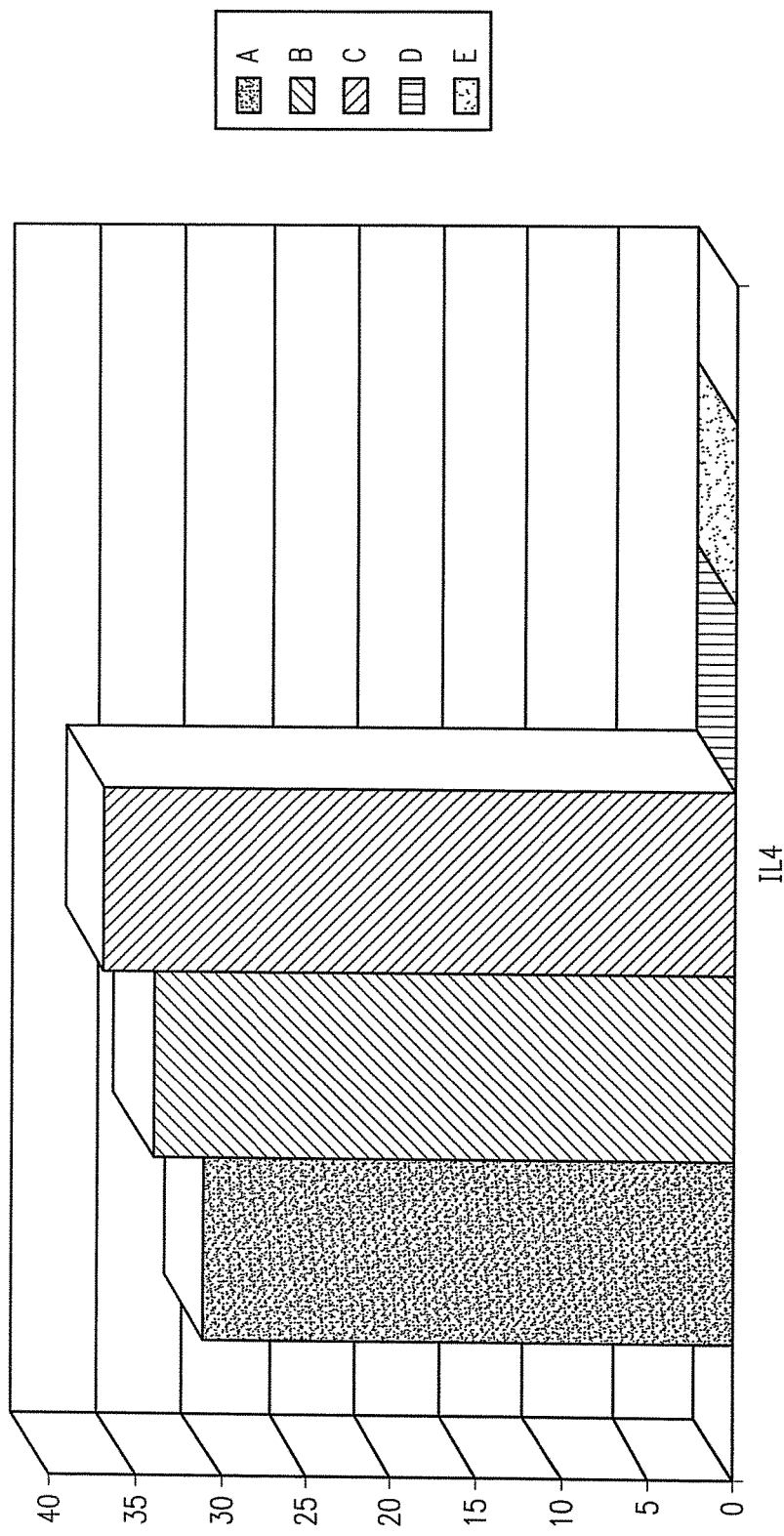
FIG. 8 shows the effect of Glucocerebroside on Serum IL-4.
Figure 9:
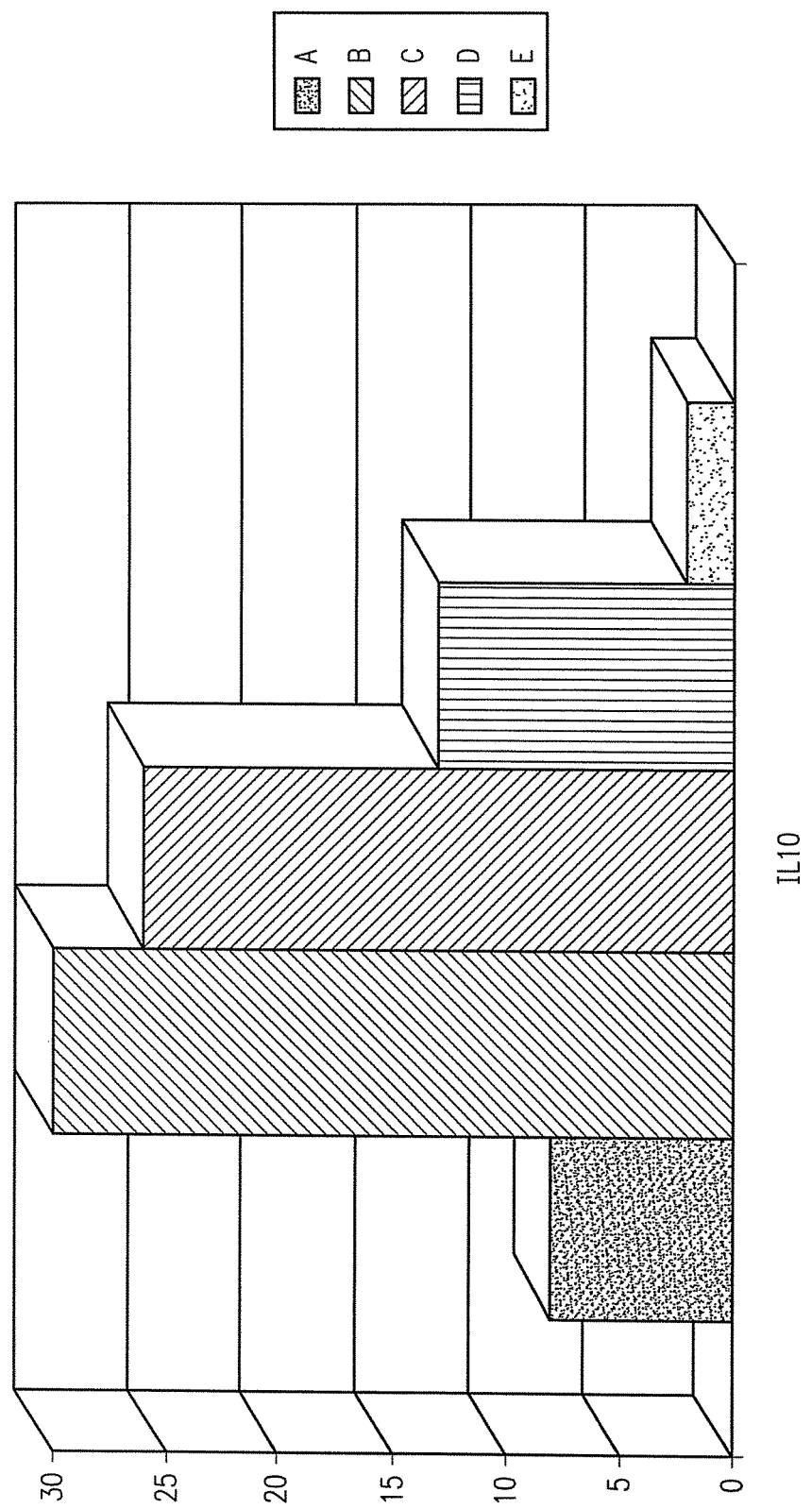
FIG. 9 shows the effect of Glucocerebroside on Serum IL10.

FIG. 5 shows that Glucocerebroside treatment significantly lowered serum IFNγ levels. Group A had approximately 3,725 pg/ml and Group C had 5,620 pg/ml. FIG. 6 shows that serum IL2 levels increased with Glucocerbroside treatment: Group A had approximately 602 pg/ml and Group C had 206 pg/ml. Serum IL12 levels, as shown in FIG. 7, also increased with Glucocerebroside: Group A had approximately 22,250 pg/ml and Group C had 10,100 pg/ml. As shown in FIGS. 8 and 9, respectively, serum IL4 and IL10 levels decreased with Glucocerebroside treatment. According to FIG. 8, Group A had a serum IL4 level of approximately 31 pg/ml and Group C had 37 pg/ml. According to FIG. 9, Group A had a serum IL10 level of approximately 8 pg/ml and Group C had 26 pg/ml.

Figure 10:
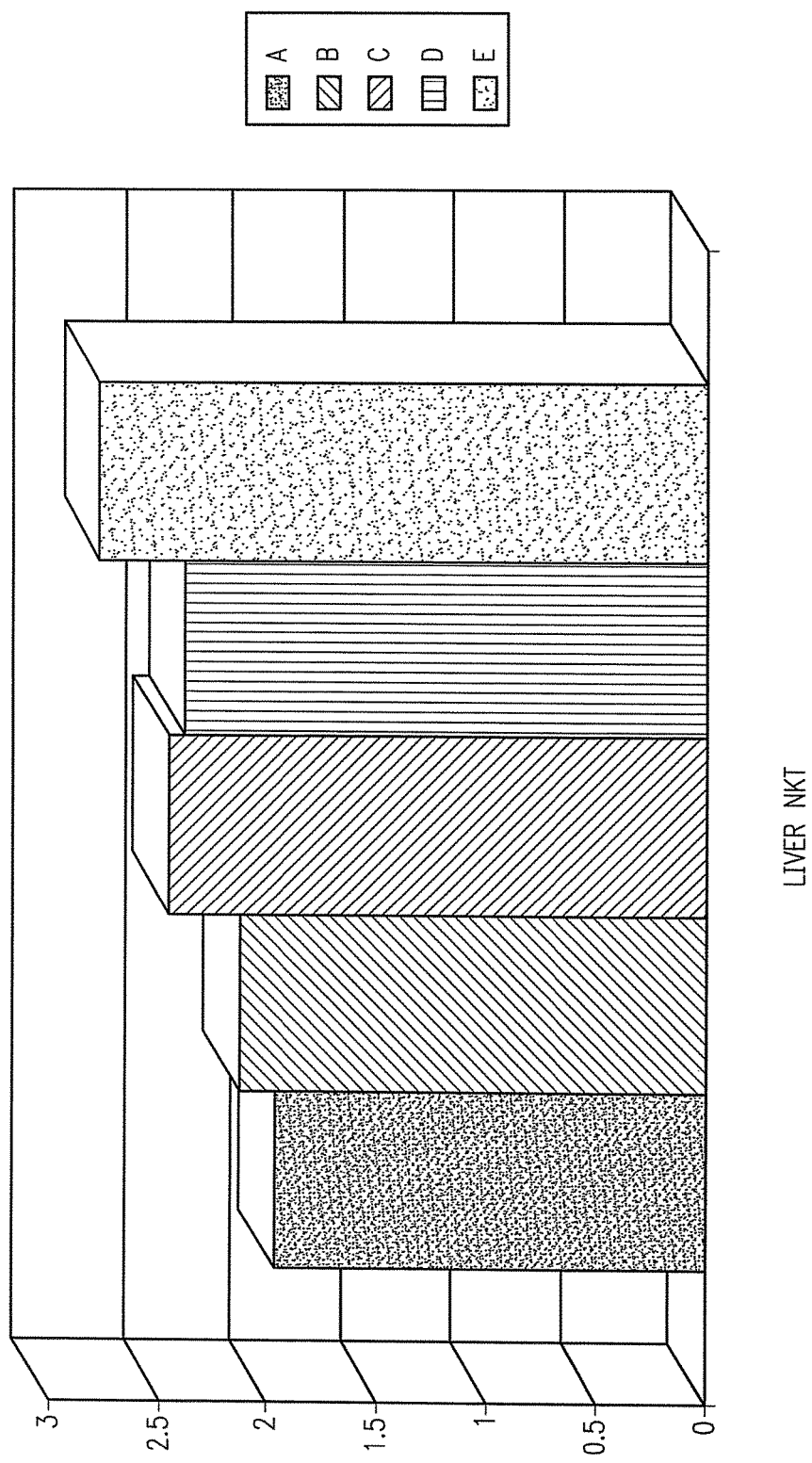
FIG. 10 shows the effect of Glucocerebroside on liver NKT cells.
Figure 11:
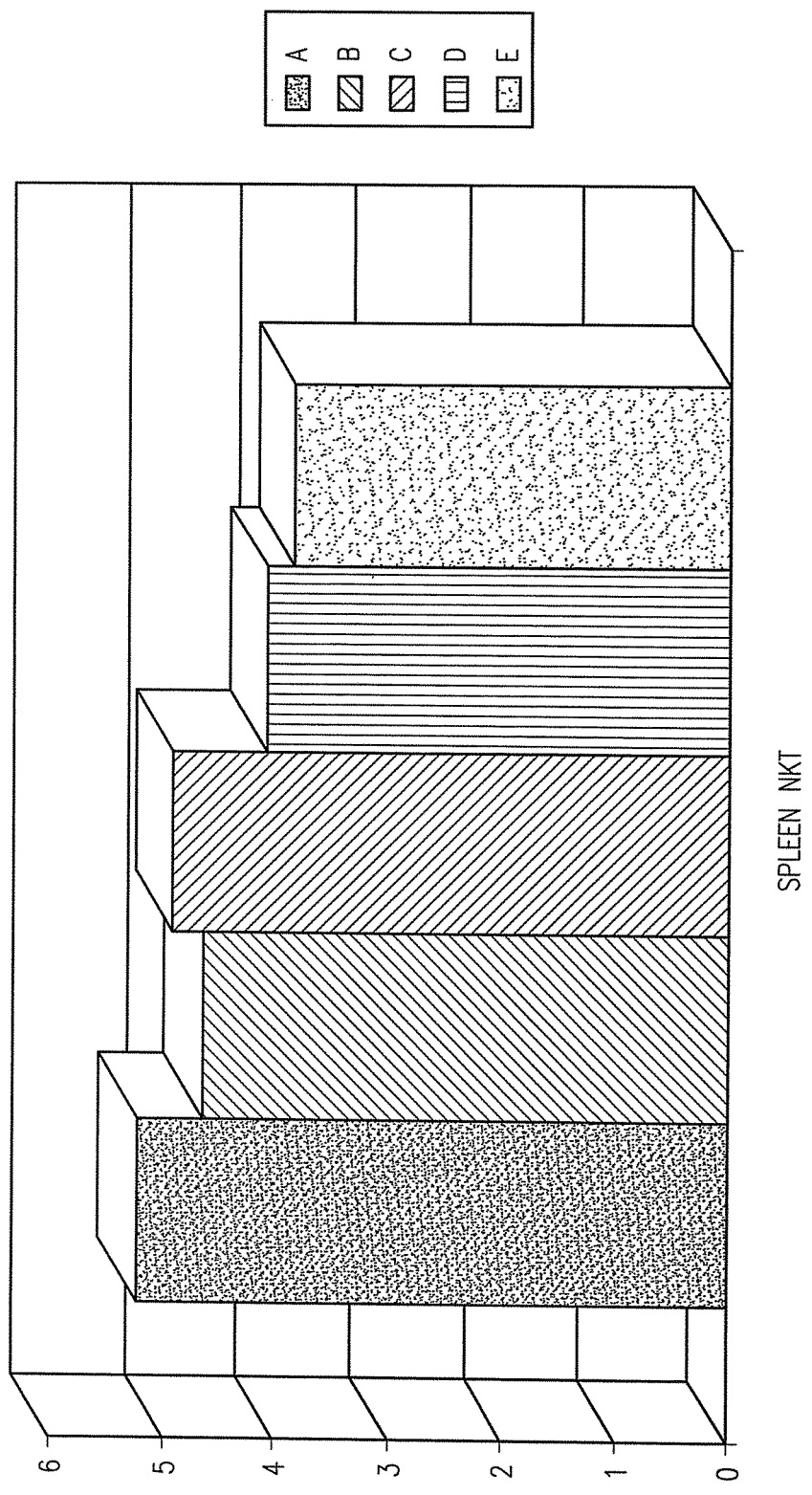
FIG. 11 shows the effect of Glucocerebroside on spleen NKT cells.

As shown in FIG. 10, the effect of Glucocerebroside on immune mediated hepatitis was associated with a significant decrease in intrahepatic NKT lymphocytes. Such a decrease did not occur with intrasplenic NKT lymphocytes (see FIG. 11).

Figure 12:
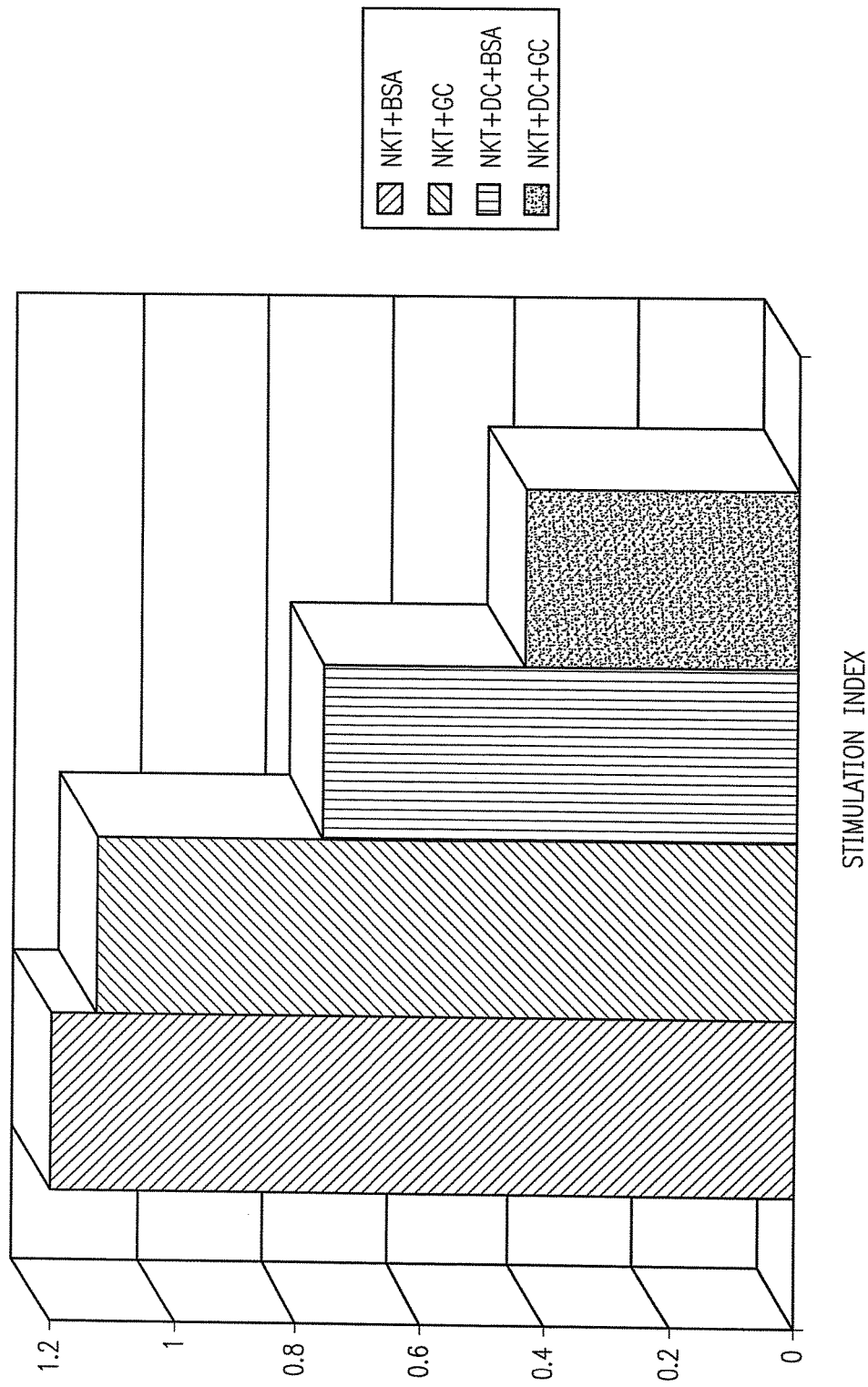
FIG. 12 shows the effect of Glucocerebroside on NKT cell proliferation in vitro.

In FIG. 12, the proliferation of NKT cells containing various components in vitro were studied. Group A contained NKT cells and BSA; Group B contained NKT cells and Glucocerebroside; Group C contained NKT cells, Dentritic Cells and BSA; and Group D contained NKT cells, Dendritic Cells and Glucocerebroside. The stimulation index decreased from Group A to Group D. This depicts that there is an overall decrease in NKT cell proliferation. The presence of Glucocerebroside and Dentritic Cells is necessary for this NKT cell decrease.

The administration of Glucocerebroside resulted in the significant amelioration of Con-A hepatitis. This effect was accompanied by a significant decrease in the IFNγ response. These results suggest that the Glucocerebroside effect may be associated with the inhibition of intrahepatic NKT cells by the competitive displacement of activating elements from the CD1d molecule.

II. Glucocerebroside Treatment of Colitis

Materials and Methods
Animals
Normal inbred 2 to 4 month old Balb/c male mice were obtained from Jackson Laboratories, USA and maintained in the Animal Core of the Hadassah-Hebrew University Medical School. Mice were maintained on standard laboratory chow and kept in 12-hour light/dark cycles.
Induction of Colitis
2,4,6-trinitrobenzene sulfonic acid (TNBS)—colitis was induced by rectal instillation of TNBS, 1 mg/mouse, dissolved in 100 ml of 50% ethanol as described. [Collins, C., et al., Eur. J. Immunol. 26:3114-3118 (1996)].
Evaluation of the Effect of Glucocerebroside on Experimental Colitis
The effect of Glucocerebroside was evaluated by monitoring the following parameters for colitis:
Clinical Assessment of Colitis:
Diarrhea was followed daily throughout the study.
Macroscopic Score of Colitis
Colitis assessment was performed 14 days following colitis induction using standard parameters [Madsen, K. L., et al., Gastroenterology 113:151-159 (1997); Trop, S., et al., Hepatology 27:746-755 (1999)].
Four macroscopic parameters were determined, namely: diarrhea, degree of colonic ulcerations; intestinal and peritoneal adhesions; and wall thickness. Each parameter was graded on a scale from 0 (completely normal) to 3 (most severe) by two experienced blinded examiners.
Grading of Histological Lesions
For histological evaluation of inflammation, distal colonic tissue (last 10 cm) was removed and fixed in 10% formaldehyde. Five paraffin sections from each mouse were then stained with hematoxylin-eosin by using standard techniques. The degree of inflammation on microscopic cross sections of the colon was graded semiquantitatively from 0 to 4 [Madsen et al., (1997) ibid.; Trop et al., Hepatology 27:746-755 (1999)]. Grade 0: normal with no signs of inflammation; Grade 1: very low level of leukocyte infiltration; Grade 2: low level of leukocyte infiltration; and Grade 3: high level of infiltration with high vascular density, and bowel wall thickening; Grade 4: transmural infiltrates with loss of goblet cells, high vascular density, wall thickening, and disruption of normal bowel architecture. The grading was performed by two experienced blinded examiners.
Splenic and Hepatic Lymphocyte Isolation
Splenocytes were isolated and red blood cells removed as previously described [Vicari, A. P., et al., Immunology Today 17(2):71 (1996)]. Intrahepatic lymphocytes were isolated from all groups of mice at the end of the study, as previously described, with some modifications [Vicari et al., (1996) ibid.; Bleicher, P. A., et al., Science 250:679-682 (1990)]. The inferior vena cava was cut above the diaphragm and the liver was flushed with 5 ml of cold PBS until it became pale. The connective tissue and the gall bladder were removed, and livers were place in a 10-ml dish in cold sterile PBS. Livers and spleens were crushed through a stainless mesh (size 60, Sigma Chemical Co., St. Louis Mo.). Cell suspension was placed in a 50 ml tube for 3 minutes and washed twice in cold PBS (1,250×rpm for 10 minutes), and debris was removed. Cells were resuspended in PBS, cell suspension was placed through a nylon mesh presoaked in PBS, and unbound cells were collected. Cells were washed twice in 45 ml PBS (1,250×rpm in room temperature). For liver and spleen lymphocyte isolation 20 ml of histopague 1077 (Sigma Diagnostics, St. Louis, Mo.) were slowly placed underneath the cells suspended in 7 ml of PBS, in a 50-ml tube. The tube was centrifuged at 1,640 rpm for 15 minutes at room temperature. Cells at the interface were collected, diluted in a 50-ml tube, and washed twice with ice-cold PBS (1,250 rpm for 10 minutes). Approximately $1 \times 10^6$ cells/mouse liver were recovered. The viability by trypan blue staining was more than 95%. Both splenocytes and liver-associated lymphocytes were isolated from all animals in all experimental groups.

FACS of Intrahepatic and Intrasplenic Lymphocytes for NKT, CD4 and CD8 Markers

Immediately following lymphocyte isolation, triplicates of $2-5 \times 10^4$ cells/500 μl PBS were put into Falcon 2052 tubes incubated with 4 ml of 1% BSA for 10 minutes, and centrifuged at 1400 rpm for 5 minutes. Analysis of lymphocyte subpopulations was performed using anti-NK1.1, anti-CD3, anti-CD4 and anti CD-8 antibodies. Cells were washed twice in 1% BSA, and kept in 4° C. until reading. For the control group, only 5 μl of 1% BSA was added. Analytical cell sorting was performed on $1 \times 10^4$ cells from each group with a fluorescence-activated cell sorter (FACSTAR plus, Becton Dickinson). Only live cells were counted, and background fluorescence from non-antibody-treated lymphocytes were deducted from the levels obtained. Gates were set on forward- and side-scatters to exclude dead cells and red blood cells. The data were analyzed with Consort 30 two-color contour plot program (Becton Dickinson, Oxnard, Calif.), or the CELLQuest program.

Measurement of Cytokine Levels

Blood was drawn from mice in all groups and centrifuged at 14,000 rpm. Serum IFN-γ, IL2, IL4, IL10 and IL-12 levels were measured by "sandwich" ELISA using Genzyme Diagnostics kits (Genzyme Diagnostics, MA).

Example 1

Glucocerebroside Amelioration of Experimental Colitis

To evaluate the immune modulatory effect of Glucocerebroside in a murine model of experimental colitis, four groups of Balb/c mice, consisting of 10 mice each were studied. Group A and Group B mice were challenged with rectal TNBS and Group C and Group D were given normal saline. Group B and Group D mice were intraperitoneally administered 1.5n of Glucocerebroside daily, for 9 days. This is summarized in Table 3.

TABLE 3

| Experimental and Control Groups | | |
|---|---|---|
| Group | TNBS | Glucocerebroside (IP 1.5 ug) |
| A | + | − |
| B | + | + |
| C | − | − |
| D | − | + |

Figure 14:
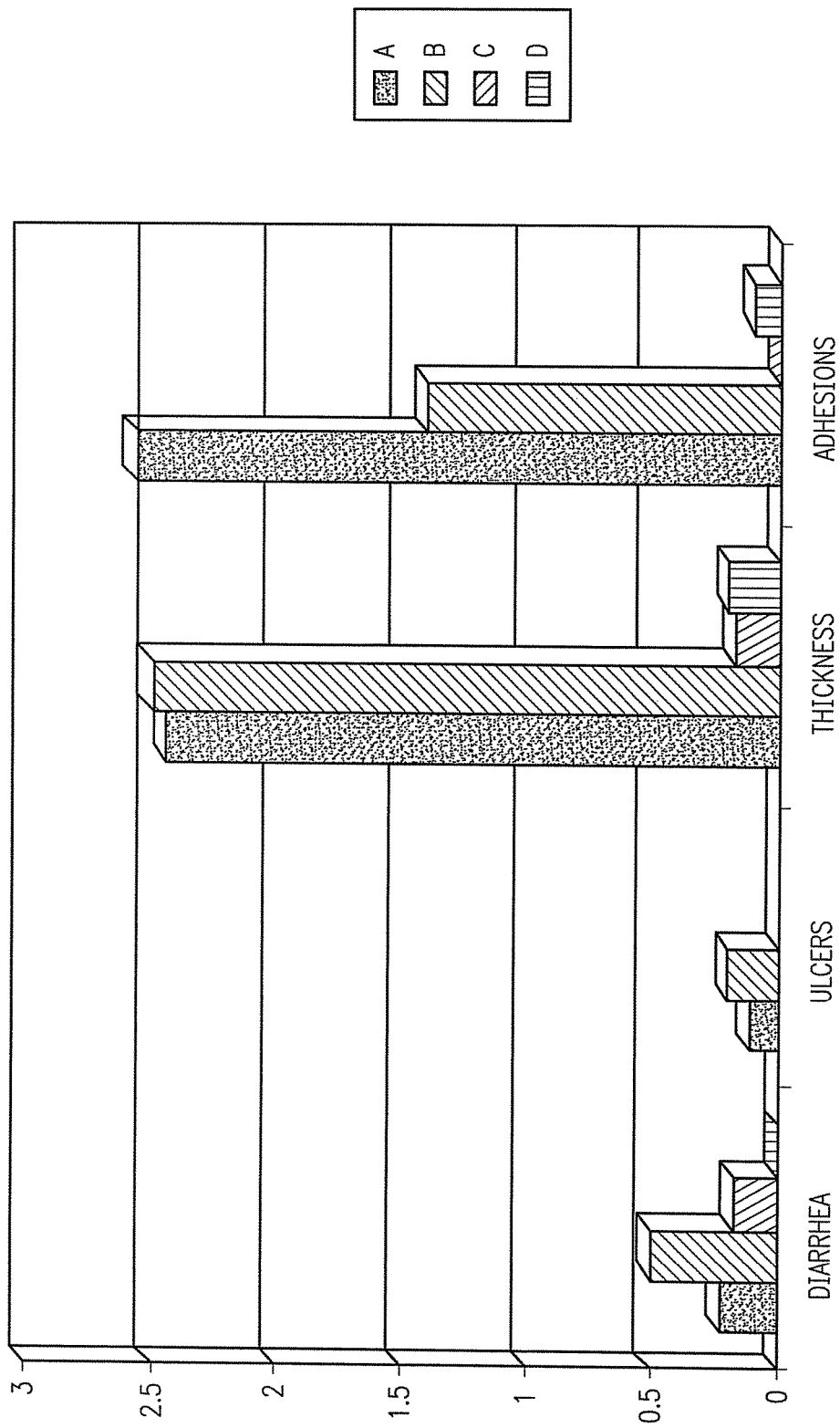
FIG. 14 shows the effect of Glucocerebroside on Macroscopic Colitis Score.

As shown in FIG. 14, treatment with Glucocerebroside showed improvement in the macroscopic colitis score for Diarrhea. Group A had a score of approximately 0.22 and Group B had a score of approximately 0.5. The score for the degree of colonic ulcerations also improved, since Group A had an approximate score of 0.11 and Group B had an approximate score of 0.2. There was also a slight improvement in macroscopic score for wall thickness, since both Group A and Group B had approximate scores of 2.44 and 2.56, respectively. However, intestinal and peritoneal adhesions increased for Group A, versus Group B, where approximate scores were 2.56 and 1.4, respectively.

Figure 15:
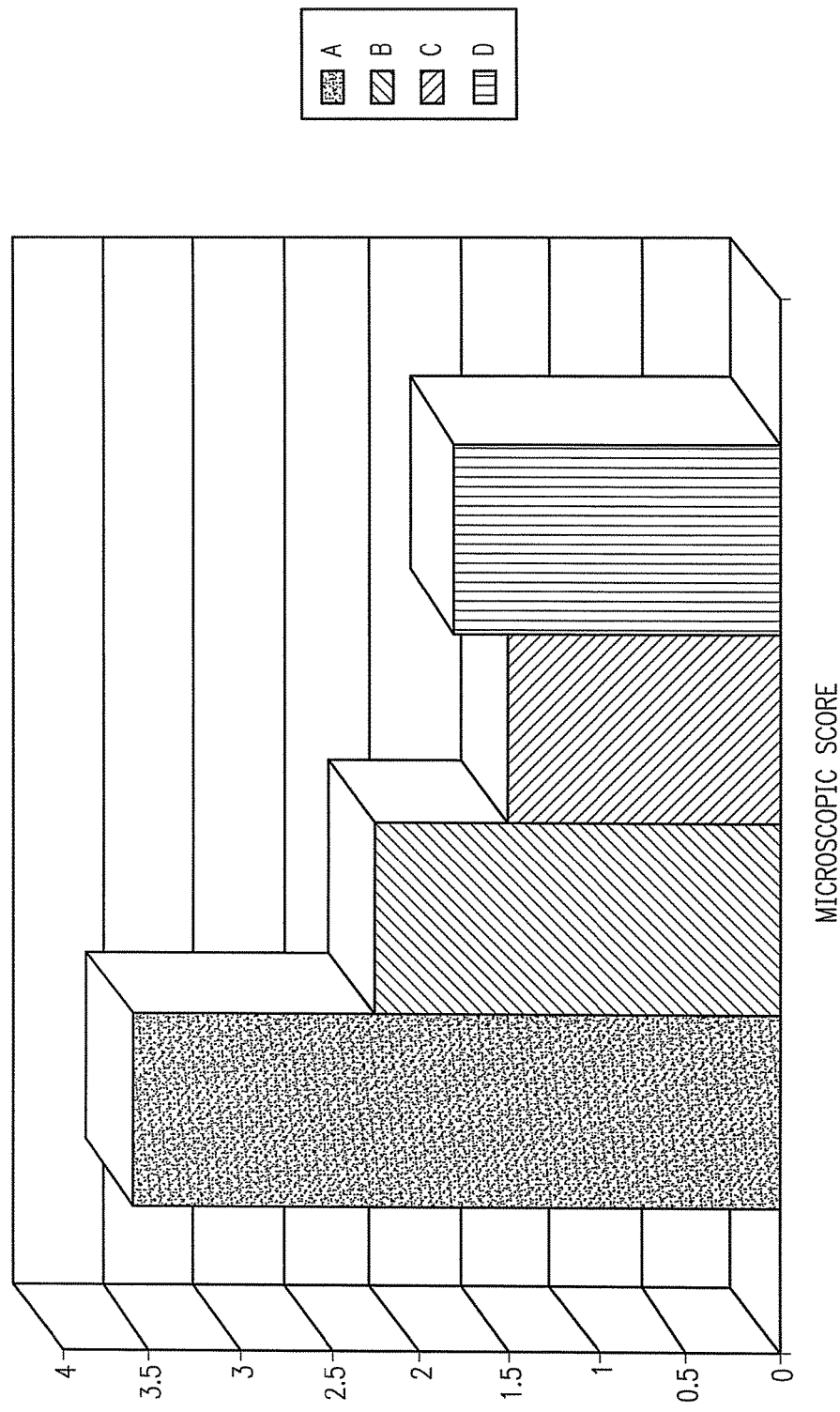
FIG. 15 shows the effect of Glucocerebroside on Microscopic Colitis Score

As shown in FIG. 13 and FIG. 15, Group A, which did not receive Glucocerebroside, had the highest microscopic colitis score of approximately 3.6, evidencing a high degree of inflammation. Group B, C and D had practically normal biopsies (lower microscopic scores).

The administration of Glucocerebroside resulted in marked alleviation of colitis, manifested by significant improvement of the macroscopic and microscopic colitis scores in Group A mice compared to Group B mice.

Figure 16:
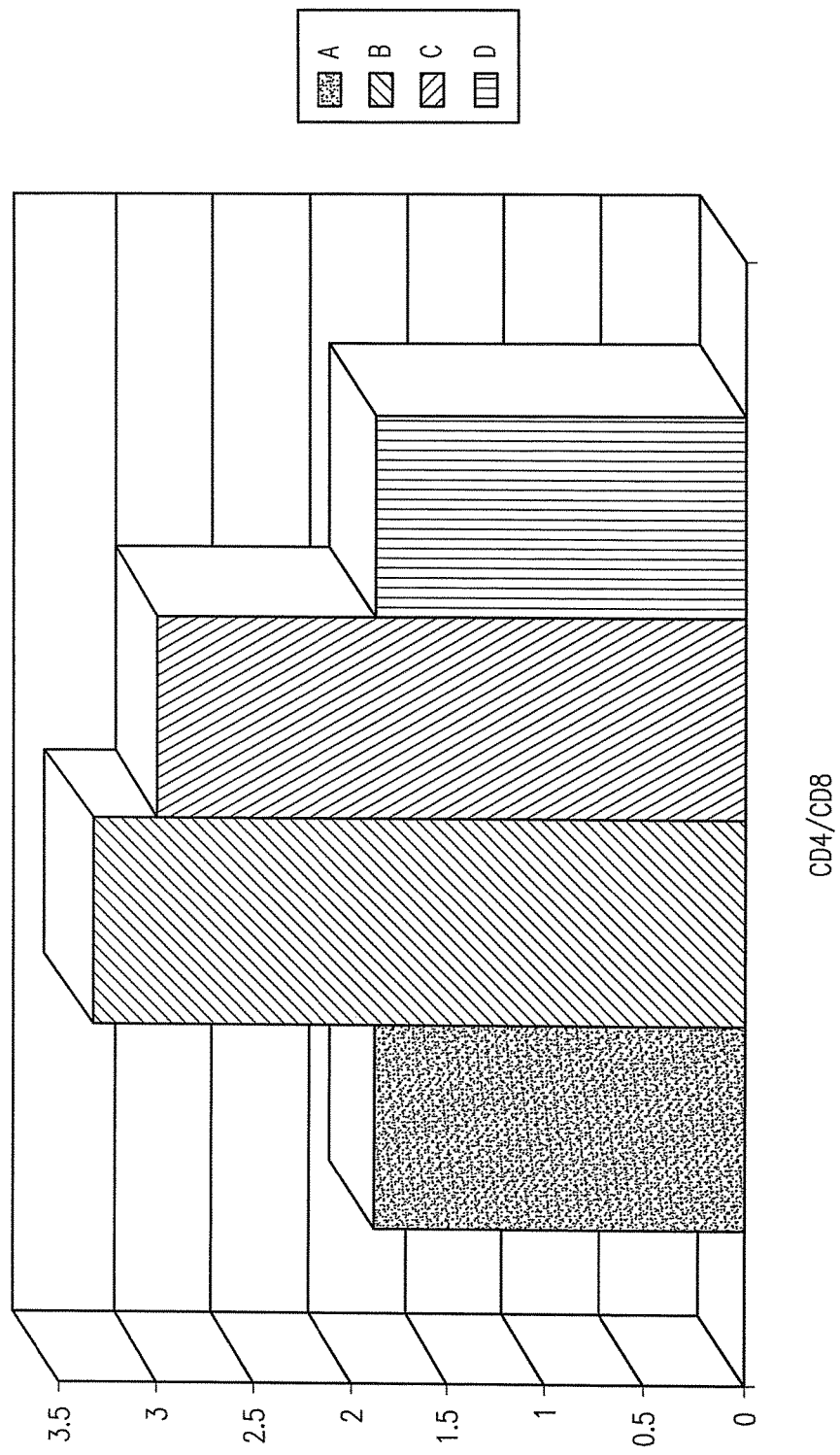
FIG. 16 shows the effect of Glucocerebroside on spleen CD4/CD8 ratio.
Figure 17:
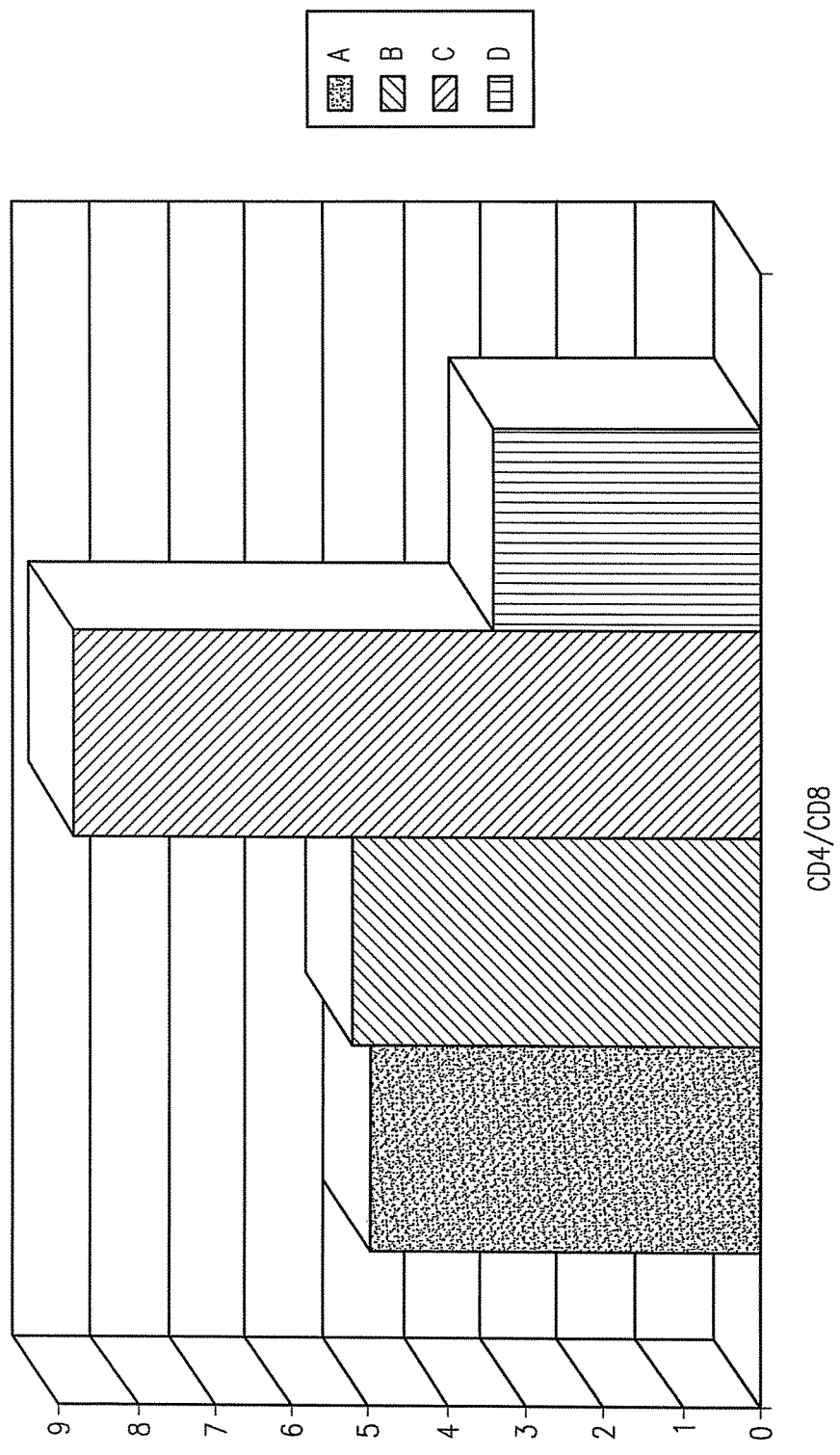
FIG. 17 shows the effect of Glucocerebroside on liver CD4/CD8 ratio.

The effect of Glucocerebroside on Group C and Group D mice showed a Spleen CD4/CD8 ratio of 3.0 and 1.89, respectively. The effect of Glucocerebroside on Group C and D mice showed a liver CD4/CD8 ratio of 8.8 and 3.4, respectively. The ratio of ratios of Group C mice (naïve animals) versus Group D mice (animals treated with Glucocerebroside) were 0.34 and 0.65, respectively. These results show a decrease in NKT cells in the periphery and the liver, and a decreased CD4/CD8 ratio in the periphery and the liver. Therefore, the effect of Glucocerebroside was more intrahepatic CD8 trapping. These results are shown in FIG. 16 and FIG. 17.

The effect of Glucocerebroside on Group A and Group B mice showed a Spleen CD4/CD8 ratio of 1.89 and 3.33, respectively. The effect of Glucocerebroside on Group A and Group B mice showed a liver CD4/CD8 ratio of 5.0 and 5.24, respectively. The ratio of ratios of Group A mice (animals with colitis not treated with Glucocerebroside) versus Group B mice (animals with colitis treated with Glucocerebroside) were 0.34 and 0.65, respectively. These results show an increase in NKT cells in the periphery and no change in NKT cells in the liver. There was an increased peripheral CD4/CD8 ratio and a mild increase of the liver CD4/CD8 ratio. These results are also shown in FIG. 16 and FIG. 17. Glucocerebroside treatment resulted in more intrahepatic CD8 trapping.

Figure 18:
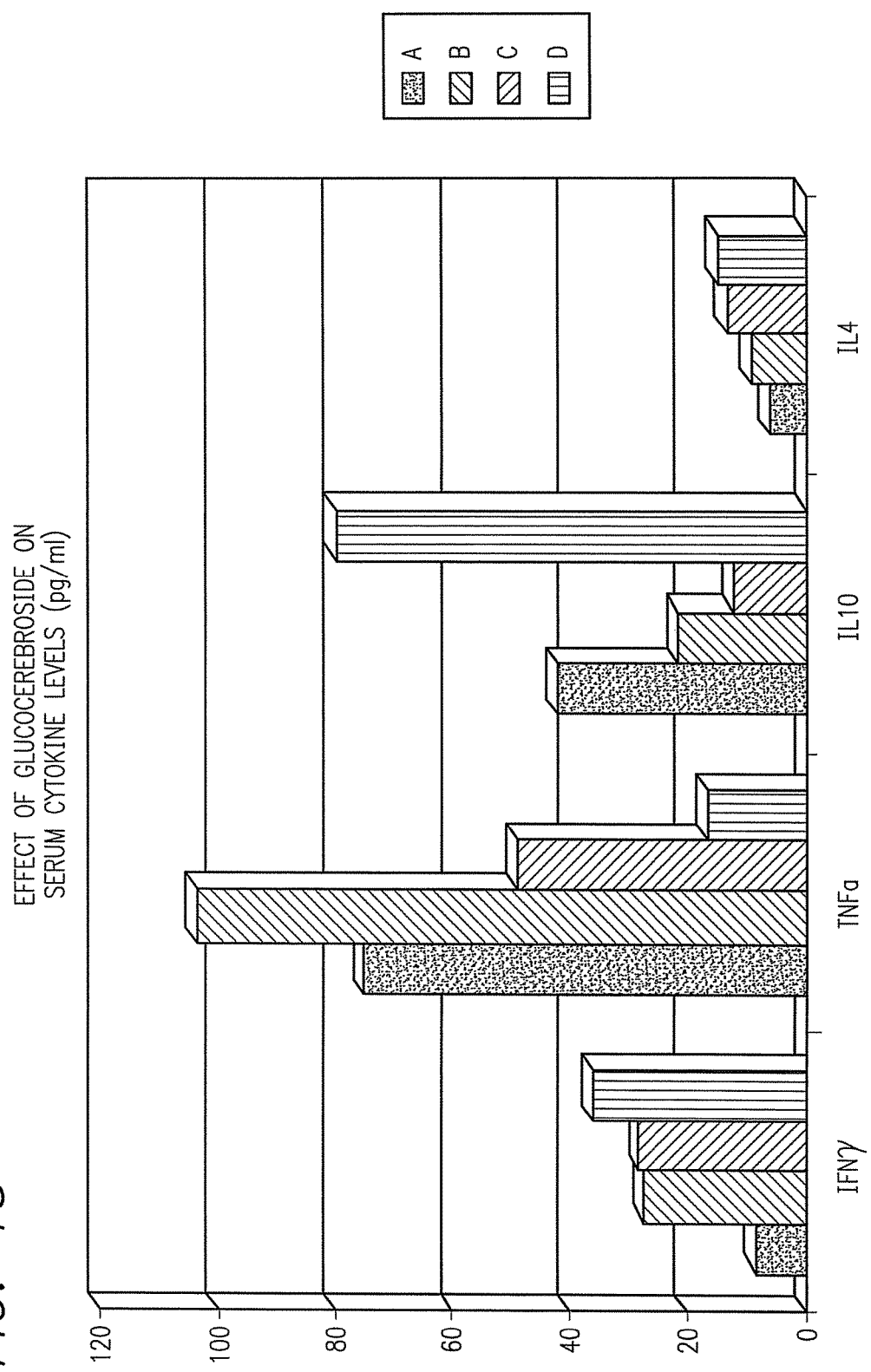
FIG. 18 shows the effect of Glucocerebroside on serum cytokine levels.

FIG. 18 shows the effect of Glucocerebroside on serum cytokine levels. Serum IFNγ levels were increased with Glucocerebroside treatment. Group A had approximately 8.3 pg/ml and Group B had approximately 27.1 pg/ml. Serum TNFa levels also increased with Glucocerbroside treatment: Group A had approximately 75 pg/ml and Group B had approximately 103.6 pg/ml. Serum IL4 levels also increased with Glucocerebroside: Group A had approximately 5.7 pg/ml and Group B had approximately 9.1 pg/ml. However, serum IL10 levels decreased with Glucocerebroside treatment. Group A had a serum IL10 level of approximately 42.1 pg/ml and Group B had approximately 21.4 pg/ml.

Alleviation of colitis by Glucocerebroside treatment was associated with a significant increase in intrahepatic CD8+ T cell trapping. The peripheral/intrahepatic CD4+/CD8+ ratio increased by 85% in Group A mice treated with Glucocerebroside versus untreated Group B mice. A similar effect was observed when Glucocerebroside was administered to naïve animals: the peripheral/intrahepatic CD4+/CD8+ ratio increased by 61% in Group C Glucocerebroside treated mice versus untreated animals. While Glucocerebroside treatment led to a 108% increase of the peripheral/intrahepatic NKT cell ratio in naïve mice, the beneficial effect of Glucocerebroside on TNBS colitis was associated with a relative decrease of this ratio.

Similar results were obtained when the same experiment was conducted with the 15 µg of Glucocerebroside, administered orally. There was a marked alleviation of colitis manifested by a significant improvement of the macroscopic and microscopic colitis scores in Group A Glucocerebroside treated mice compared to the untreated Group B mice, as shown in Table 4.

TABLE 4

Microscopic and Macroscopic Results of the Oral Administration of Glucocerebroside for the Treatment of Colitis

| Mouse No. | A (TNBS) | B (TNBS + 15 µgGC) | C (Naïve) | D (Naïve + 150 µgGC) |
|---|---|---|---|---|
| Microscopic ||||| 
| 1 | 3 | 0.5 | 0.5 | 1 |
| 2 | 3.5 | 1.5 | 1.5 | 1 |
| 3 |  | 0.5 |  | 0.5 |
| 4 | 2 |  | 0.5 | 2 |
| 5 | 4 | 1.5 | 1.5 | 0 |
| 6 | 2 | 1.5 | 0.5 | 0 |
| 7 | 2.5 | 0 | 0.5 | 0.5 |
| 8 | 4 |  | 1 | 0 |
| 9 |  | 2 | 0.5 | 0 |
| 10 |  |  | 2 | 1 |
| Macroscopic ||||| 
| 1 | 0 | 0.5 | 0 | 0.5 |
| 2 | 0.5 | 0 | 0 | 0.5 |
| 3 | 1 | 0.5 | 0 | 0 |
| 4 | 1.5 | 0.5 | 0 | 0 |
| 5 | 1.5 | 0.5 | 0 | 0 |
| 6 | 3.5 | 0.5 | 0 | 0 |
| 7 | 2.5 | 0.5 | 0 | 0 |
| 8 |  | 0 | 0 | 0 |
| 9 |  | 0 | 0 | 0 |
| 10 |  | 0 | 0 | 0 |

III. Glucocerebroside Treatment of Non-Alcoholic Steatohepatitis

Materials and Methods
Animals

Ten-week-old male leptin-deficient C57BL/6J mice and lean C57BL/6 mice were purchased from Harlan laboratories and maintained in the Animal Core of the Hadassah-Hebrew University Medical School. Mice were fed standard laboratory chow and kept in 12-hour light/dark cycles.

Glucose Tolerance Test

Glucose tolerance was assessed by oral administration of glucose (1 gram per kilogram body weight). Blood drawn from the tail was measured for glucose at 0', 15', 30', 60', 90', 120' and 180'. Glucose levels were measured with Elite glucose test strips and a glucometer.

Hepatic MRI Measurement of Fat Content

Hepatic fat content was measured using a double-echo chemical shift gradient-echo magnetic resonance imaging (MRI) sequence that provides in-phase and opposed-phase images in a single acquisition for assessment/quantification of fat in mouse liver. The T1-weighted opposed-phase MR imaging technique is sensitive for detection of relatively small amounts of tissue fat. MRI images were performed with a 1.5-T system (Signa LX; GE, Milwaukee, USA). Double-echo MR imaging was performed with a repetition time (TR) of 125 msec, double echo times (TEs) of 4 and 6.5 msec, and a flip angle of 80°. Imaging parameters included section thickness of 3 mm, 13-cm field of view, 256*160 matrix, and one signal acquired, with use of a knee coil. Transverse (axial) and coronal images were acquired at the level of the liver with a 3 mm section thickness and no intersection gap. Quantitative assessment of signal intensity (SI) measurements of SI changes between in-phase and opposed-phase images was computed as described in previous reports (Mitchell D G et al., Invest. Radiol 26:1041-1052 (1991); Tomohiro N et al., Radiology 218:642-646 (2001)). The SI index was calculated as follows: SI index= $(SI_{ip}-SI_{op})/SI_{ip}$, where $SI_{ip}$ is SI on in-phase images and $SI_{op}$ is SI on opposed-phase images. The SI index reflects the fraction of SI loss on opposed phase images compared with the SI on in-phase images.

Example 1

Effect of Glucocerebroside on Diabetes

To evaluate the effect of Glucocerebroside on the various metabolic and immunologic components of the NASH model, four groups of C57bl mice, consisting of 12 mice each were studied. As shown in Table 5, Group A and Group B mice were ob/ob mice, whereas Group C and Group D mice were not. Group A and Group C mice were injected intraperitoneally with 1.5 µg in 100 µl PBS every other day for 14 days. Group B and Group D naïve ob/ob mice and naïve C57bl mice, respectively, were left untreated.

TABLE 5

Experimental and Control Groups

| | |
|---|---|
| A | OB/OB MICE INJECT WITH GLUCOCEREBROSIDE IP 1.5 µg/mouse in 100 µl PBS every other day |
| B | Naive OB/OB MICE untreated |
| C | C57bl INJECT WITH GLUCOCEREBROSIDE IP 1.5 µg/mouse in 100 µl PBS every other day |
| D | Naive C57bl untreated |

Figure 19:
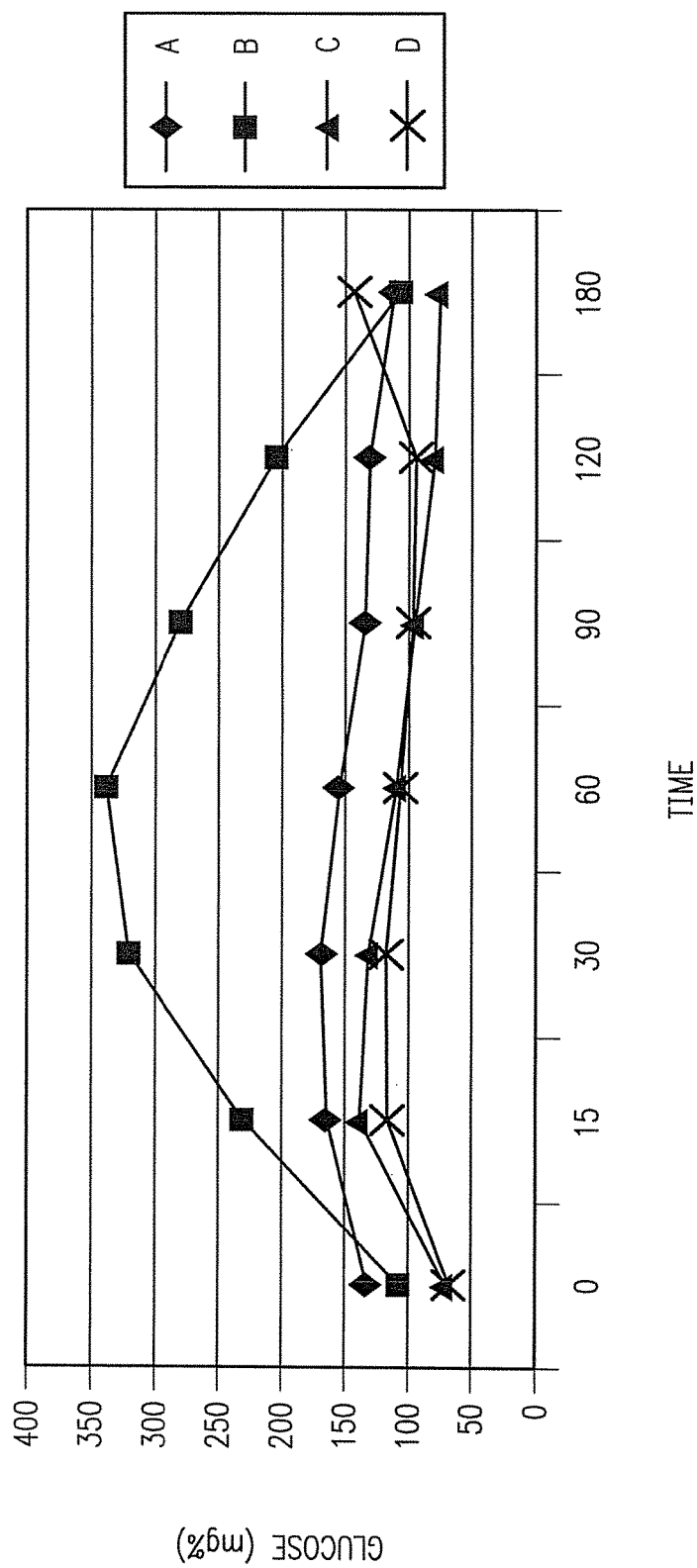
FIG. 19 shows a Glucose Tolerance Test for Glucocerebroside treatment.

On the 14th day, glucose tolerance tests were performed on 6 mice from each group. As depicted in FIG. 19, Group A mice, which were treated with Glucocerebroside, had a higher glucose tolerance than naïve ob/ob mice that were not treated. This suggests that Glucocerebroside injection alters the metabolic profile of ob/ob mice, improving their glucose tolerance results, rendering them less diabetic.

Example 2

Effect of Orally Administered Glucocerebroside on NASH

To evaluate the effect of Glucocerebroside on the various metabolic and immunologic components of the NASH model, four groups of C57bl mice, consisting of 12 mice each were studied. As shown in Table 6, Group A and Group B mice were ob/ob mice, whereas Group C and Group D mice were not. Group A and Group C mice were injected intraperitoneally with 1.5 µg in 100 µl PBS every other day for 14 days. Group B and Group D naïve ob/ob mice and naïve C57bl mice, respectively, were left untreated.

TABLE 6

Experimental and Control Groups

| | |
|---|---|
| A | OB/OB MICE FEED GLUCOCEREBROSIDE 15 µg/mouse in 100 µl PBS every other day |
| B | Naive OB/OB MICE untreated |
| C | C57bl FEED GLUCOCEREBROSIDE 15 µg/mouse in 100 µl PBS every other day |
| D | Naive C57bl untreated |

Figure 20:
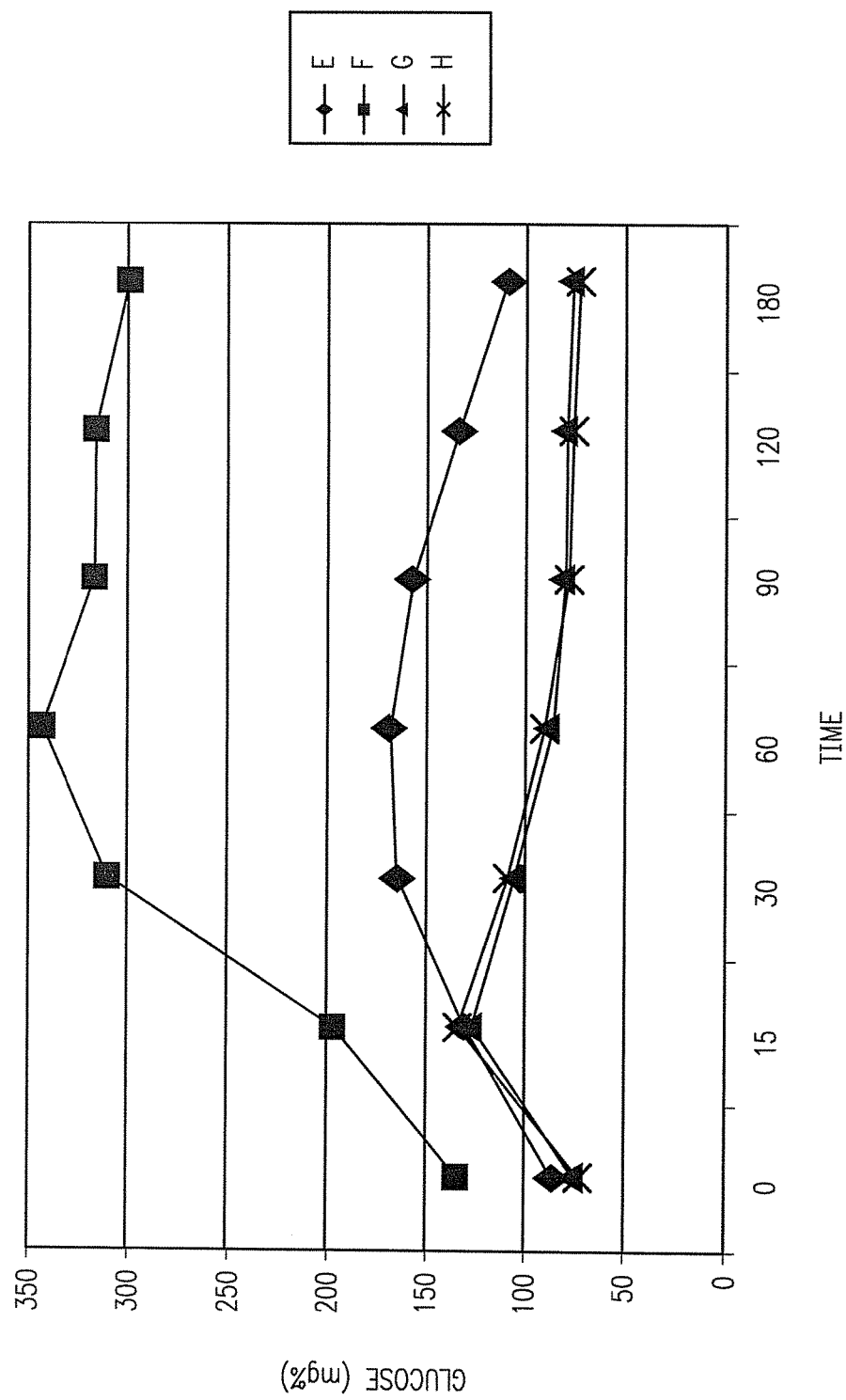
FIG. 20 shows a Glucose Tolerance Test for Glucocerebroside treatment.

On the 14$^{th}$ day, glucose tolerance tests were performed on 6 mice from each group. As depicted in FIG. 20, Group A mice, which were treated with Glucocerebroside, had a higher glucose tolerance than naïve ob/ob mice that were not treated. This suggests that immune modulation through oral immune regulation induction alters the metabolic profile of ob/ob mice, improving their glucose tolerance results, rendering them less diabetic.

Example 3

The Effect of Glucocerebroside on the Hepatic Fat Content

To determine the effect of Glucocerebroside on the various metabolic and immunologic components of the NASH model, four groups of C57bl mice, consisting of 12 mice each were studied. As shown in Table 7, Group A and Group B mice were ob/ob mice, whereas Group C and Group D mice were not. Group A and Group C mice were injected intraperitoneally with 1.5 µg in 100 µl PBS every other day for 14 days. Group B and Group D naïve ob/ob mice and naïve C57bl mice, respectively, were left untreated.

TABLE 7

Experimental and Control Groups

| | |
|---|---|
| A | OB/OB MICE INJECT WITH GLUCOCEREBROSIDE IP 1.5 µg/mouse in 100 µl PBS every other day |
| B | Naive OB/OB MICE untreated |
| C | C57bl INJECT WITH GLUCOCEREBROSIDE IP 1.5 µg/mouse in 100 µl PBS every other day |
| D | Naive C57bl untreated |

To determine hepatic fat content, mice of all four groups underwent an abdominal MRI on day 14 of the experiment (Table 8). Hepatic fat content was determined and was described as the SI index (IP-OP/IP). Liver size, in area, was also determined. The results showed a reduction in liver fat content due to Glucocerebroside treatment. Group A mice treated with Glucocerebroside had an SI index of 0.46, as compared to Group B, which had an SI index of 0.54. There was also a reduction in liver size resulting form Glucocerebroside treatment. Glucocerebroside treated Group A mice had a liver area of 20.14, as compared to Group B, which had a liver area of 24.2.

TABLE 8

Calculated MRI Hepatic Fat Content of the Six Mice Groups

| | In Phase Images | Opposite Phase Images | FAT CONTENT (IP – OP) | SI INDEX (IP – OP/IP) | Area |
|---|---|---|---|---|---|
| Fat | 536 | 351 | 185 | 0.35 | 25 |
| | 603 | 293 | 310 | 0.51 | 16 |
| | 575 | 251 | 324 | 0.56 | 20.5 |
| | 554 | 234 | 320 | 0.58 | 23.5 |
| | 520 | 202 | 378 | 0.61 | 30.5 |
| | 560 | 201 | 359 | 0.64 | 28.5 |
| Average Fat + Tx | | | | 0.54 | 24.2 |
| | 514 | 279 | 235 | 0.46 | 13.5 |
| | 527 | 256 | 271 | 0.51 | 20 |
| | 574 | 305 | 269 | 0.47 | 26 |
| | 561 | 344 | 217 | 0.39 | 18.5 |
| | 462 | 283 | 179 | 0.39 | 21.5 |
| | 579 | 309 | 270 | 0.47 | 27.5 |
| | 1132 | 502 | 629 | 0.56 | 14 |
| Average Thin | | | | 0.464286 | 20.14286 |
| | 518 | 423 | 95 | 0.18 | 10.5 |
| | 517 | 434 | 83 | 0.16 | 11.5 |
| | 476 | 397 | 79 | 0.17 | 11.5 |
| | 1040 | 813 | 227 | 0.22 | 10 |
| | 892 | 731 | 161 | 0.18 | 10 |
| Average Thin + Tx | | | | 0.18 | 10.7 |
| | 547 | 479 | 68 | 0.12 | 16.5 |
| | 443 | 424 | 19 | 0.04 | 14 |
| | 472 | 409 | 63 | 0.13 | 8 |
| | 507 | 440 | 67 | 0.13 | 16.5 |
| | 532 | 438 | 94 | 0.18 | 5.5 |
| | 534 | 481 | 53 | 0.1 | 10 |
| | 987 | 871 | 117 | 0.12 | 15 |
| | 974 | 839 | 135 | 0.14 | 13.5 |
| | 930 | 870 | 60 | 0.06 | 9 |
| | 302 | 787 | 115 | 0.13 | 8 |
| | 927 | 889 | 40 | 0.04 | 15 |
| | 910 | 887 | 23 | 0.03 | 10 |
| Average | | | | 0.1 | 11.75 |

This suggests that Glucocerebroside alters the metabolic profile in a way which results in a reduction in the rate of fat accumulation and NASH in the livers of susceptible mammals.

IV. Glucocerebroside Treatment of Melanoma

Materials and Methods
Animals
Four groups of C57bl mice were studied.
Histology Examination
Histological sections of the lungs from mice were examined to determine the degree of lung damage. For each mouse a single lung segment was fixed in 10% buffered formaldehyde and embedded in paraffin for histologic analysis. Sections were stained with hematoxylin/eosin and histologic evaluation was performed.

Example 1

Effect of Glucocerebroside Treatment on Melanoma

To evaluate the effect of Glucocerebroside on melanoma, four groups of C57bl mice, consisting of 8 mice each were studied. Group A and Group B were subcutaneously administered 1×10$^6$ cells of the B16 melanoma cell line and Group C and Group D were intravenously treated with 1×10$^5$ cells of the B16 melanoma cell line to induce melanoma. Group A and Group C were treated with 1 µg of Glucocerebroside intraperitoneally, every day, skipping the last two days of every week, starting on the second day of the first week. Group B and Group D mice were given saline only. This is summarized in Table 9.

TABLE 9

| Experimental and Control Group | | |
|---|---|---|
| Group: | | Melanoma |
| A | GC treatment | SC |
| B | SALINE | SC |
| C | GC treatment | IV |
| D | SALINE | IV |

Figure 21:
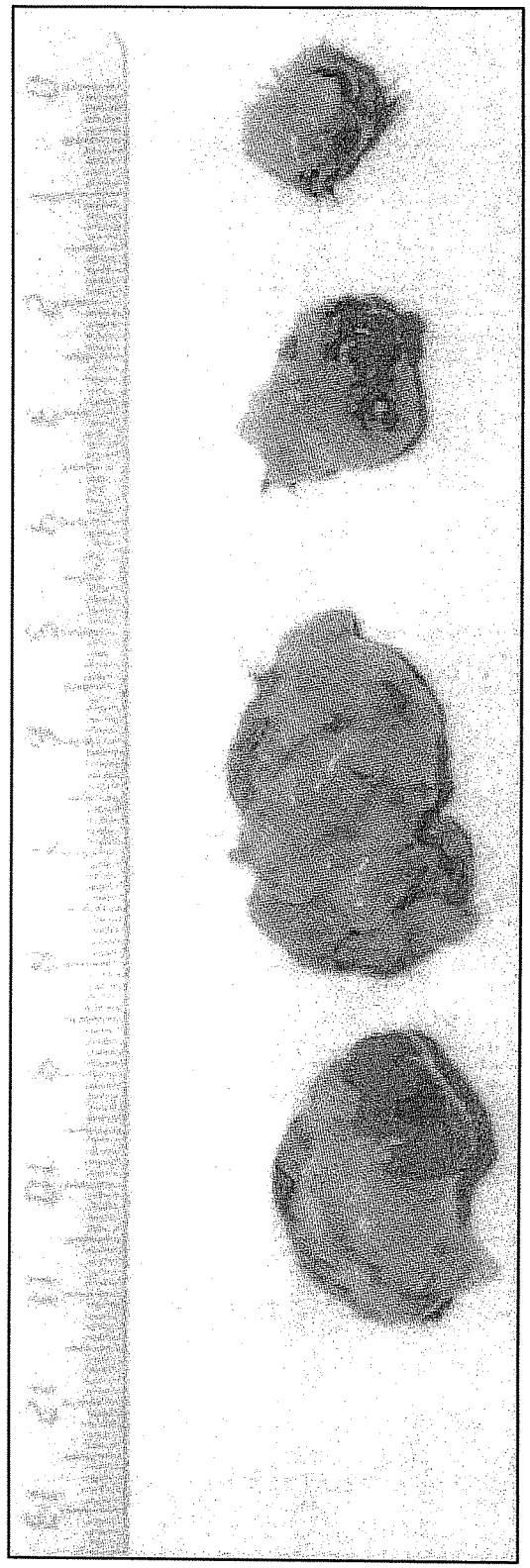
FIG. 21 shows the effect of Glucocerebroside on tumor size.

Treatment with Glucocerebroside significantly ameliorated tumor size. Tumors were removed and subsequently measured. The average tumor weight in Group A was 1.63+/−0.82 g, and the average tumor weight in Group B was 2.89+/−0.01 g. The differences in tumor size can be seen in FIG. 21.

Treatment with Glucocerebroside also showed a decrease in lung metastasis. Lung cells of Group C and Group D were fixed for histological analysis. The average number of lung metastasis in Group C was 3+/−1 per lung and the mean number of lung metastasis in Group D was 8+/−3 per lung.

The invention claimed is:

1. A method for the treatment of a disease in a mammalian subject comprising:
   administering to said subject an effective amount of a mammalian intermediary metabolite,
   wherein said intermediary metabolite is a glycosylceramide,
   wherein said disease is nonalcoholic steatohepatitis, and
   wherein said administration improves the non-alcoholic steatohepatitis in said mammalian subject.

2. The method of claim 1, wherein said glycosylceramide is a glucosylceramide or galactosylceramide.

3. The method of claim 1, wherein said administering step comprises oral, intravenous, intraperitoneal, intramuscular, parenteral, transdermal, intravaginal, intranasal, mucosal, sublingual, topical, rectal or subcutaneous administration, or any combination thereof.

4. The method of claim 1, wherein said glycosylceramide is a monosaccharide ceramide.

5. The method of claim 1, wherein said mammalian subject is a human.

6. The method of claim 1, wherein said improvement in the non-alcoholic steatohepatitis in said mammalian subject comprises one or both of a reduction in hepatic fat content and a reduction in liver size.

7. The method of claim 6, wherein said mammalian subject is a human.

8. The method of claim 2, wherein the glycosylceramide consists of beta-glucosylceramide.

9. The method of claim 6, wherein the glycosylceramide consists of beta-glucosylceramide.

10. The method of claim 7, wherein the glycosylceramide consists of beta-glucosylceramide.

11. The method of claim 3, wherein said administering step consists of intravenous, intraperitoneal, intramuscular, parenteral, subcutaneous administration, or any combination thereof.

12. The method of claim 6, wherein said administering step consists of intravenous, intraperitoneal, intramuscular, parenteral, subcutaneous administration, or any combination thereof.

13. The method of claim 7, wherein said administering step consists of intravenous, intraperitoneal, intramuscular, parenteral, subcutaneous administration, or any combination thereof.

14. The method of claim 8, wherein said administering step consists of intravenous, intraperitoneal, intramuscular, parenteral, subcutaneous administration, or any combination thereof.

15. The method of claim 9, wherein said administering step consists of intravenous, intraperitoneal, intramuscular, parenteral, subcutaneous administration, or any combination thereof.

16. The method of claim 10, wherein said administering step consists of intravenous, intraperitoneal, intramuscular, parenteral, subcutaneous administration, or any combination thereof.

* * * * *